(12) United States Patent
Rocchi et al.

(10) Patent No.: US 10,105,384 B2
(45) Date of Patent: Oct. 23, 2018

(54) NUCLEIC ACIDS TARGETING TCTP FOR USE IN THE TREATMENT OF CHEMO- OR HORMONE-RESISTANT CANCERS

(71) Applicants: Palma Rocchi, Marseilles (FR); Virginie Baylot, Marseilles (FR); Julie Acunzo, Marseilles (FR); Claudia Andrieu, Marseilles (FR); Maria Katsogiannou, Marseilles (FR)

(72) Inventors: Palma Rocchi, Marseilles (FR); Virginie Baylot, Marseilles (FR); Julie Acunzo, Marseilles (FR); Claudia Andrieu, Marseilles (FR); Maria Katsogiannou, Marseilles (FR)

(73) Assignees: INSTITUT NATIONAL DE LA SANTE ET DE LA RECHERCHE MEDICALE (INSERM), Paris (FR); UNIVERSITE DE LA MEDITERRANEE AIX-MARSEILLE II, Marseille (FR)

( * ) Notice: Subject to any disclaimer, the term of this patent is extended or adjusted under 35 U.S.C. 154(b) by 0 days.

(21) Appl. No.: 14/688,499

(22) Filed: Apr. 16, 2015

(65) Prior Publication Data

US 2015/0216891 A1 Aug. 6, 2015

Related U.S. Application Data

(62) Division of application No. 13/994,862, filed as application No. PCT/EP2011/073186 on Dec. 19, 2011, now Pat. No. 9,034,840.

(30) Foreign Application Priority Data

Dec. 17, 2010 (EP) .................................... 10306447

(51) Int. Cl.
*C07H 21/04* (2006.01)
*A61K 31/7088* (2006.01)
*C12N 15/113* (2010.01)
*A61K 31/337* (2006.01)
*A61K 31/713* (2006.01)
*A61K 39/395* (2006.01)
*A61K 45/06* (2006.01)
*A61N 5/10* (2006.01)

(52) U.S. Cl.
CPC ........ *A61K 31/7088* (2013.01); *A61K 31/337* (2013.01); *A61K 31/713* (2013.01); *A61K 39/39558* (2013.01); *A61K 45/06* (2013.01); *A61N 5/10* (2013.01); *C12N 15/113* (2013.01); *C12N 15/1135* (2013.01); *C12N 2310/11* (2013.01); *C12N 2310/14* (2013.01)

(58) Field of Classification Search
CPC ..................................................... C07H 21/04
See application file for complete search history.

(56) References Cited

U.S. PATENT DOCUMENTS

| 5,610,036 | A  | * | 3/1997 | Miura ................. | C07K 14/765 435/254.23 |
|---|---|---|---|---|---|
| 7,250,289 | B2 | * | 7/2007 | Zhou .................. | C12Q 1/6837 435/287.2 |
| 7,592,323 | B1 |   | 9/2009 | Gleave | |
| 7,691,997 | B2 | * | 4/2010 | Khvorova ............ | A61K 31/713 536/24.5 |
| 7,901,882 | B2 | * | 3/2011 | Cao ...................... | C12Q 1/6837 435/6.12 |
| 2002/0177692 | A1 |   | 4/2002 | Bartel | |
| 2004/0087531 | A1 | * | 5/2004 | Telerman ........... | A61K 31/7105 514/44 A |
| 2005/0020521 | A1 | * | 1/2005 | Rana ................... | C07D 213/69 514/44 A |

* cited by examiner

*Primary Examiner* — Kimberly Chong
(74) *Attorney, Agent, or Firm* — Whitham & Cook, P.C.

(57) ABSTRACT

The present invention concerns a TCTP antagonist, in particular a nucleic acid targeting an m RNA encoding Translationally-Controlled Tumor Protein (TCTP), wherein said nucleic acid is capable of reducing the amount of TCTP in cells, for use in the treatment or prevention of hormone-independent cancer or chemo-resistant cancer, such as an androgen-independent prostate cancer.

12 Claims, 17 Drawing Sheets

Specification includes a Sequence Listing.

NUCLEIC ACIDS TARGETING TCTP FOR USE IN THE TREATMENT OF CHEMO- OR HORMONE-RESISTANT CANCERS

CROSS-REFERENCE TO RELATED APPLICATIONS

This application is application is a divisional application of USSN 13/994,862 filed Jun. 17, 2013, now U.S. Pat. No. 9,034,840, which itself was a Rule 371 national stage filing from PCT/EP2011/073186 filed Dec. 19, 2011 with a claim of priority to European Application 10306447.3 filed Dec. 17, 2010.

The present invention concerns a TCTP antagonist, in particular a nucleic acid targeting an mRNA encoding Translationally-Controlled Tumor Protein (TCTP), wherein said nucleic acid is capable of reducing the amount of TCTP in cells, for use in the treatment or prevention of hormone-independent cancer or chemo-resistant cancer, such as an androgen-independent prostate cancer.

Prostate cancer (PC) is the most common non-cutaneous malignancy among men in the Western world. After lung cancer, PC is the second most common cause of cancer-related mortality in men being responsible for approximately 13% of all cancer deaths. Although patients with localized disease may be treated by surgery or radiation, androgen ablation is usually the initial therapy in patients with advanced or metastatic disease. Unfortunately, the disease gradually progresses to a metastatic castration-resistant (CR) state, which remains incurable. During this state, tumor growth proceeds in the absence of androgens, resulting in death within 2 to 3 years after diagnosis.

Since most of the patients ultimately become unresponsive, and relapse within 2-3 years with a castration-resistant prostate cancer (CRPC), efforts have focused on the development of non-hormonal therapies targeting castration-resistant (CR) cells.

Until recently, chemotherapy failed to demonstrate a survival benefit and had only a palliative role for men with CRPC. The efficacy of docetaxel in metastatic CRPC has been shown. However, the median overall survival was prolonged for only a few months, highlighting the need for new therapies.

Therefore, there is a need in the art for efficient treatments of prostate cancer, in particular of CRPC.

DESCRIPTION OF THE INVENTION

The inventors have identified that Translationally-Controlled Tumor Protein (TCTP) binds to Heat Shock Protein 27 (Hsp27) and that TCTP is thereby protected from its ubiquitin-proteasome pathway. Inhibition of the TCTP-Hsp27 interaction leads to TCTP protein degradation.

Hsp27 was previously reported to be highly over-expressed in castration resistant prostate cancer (CRPC). The inventors have now shown that Hsp27 has a cytoprotective effect on cancer cells, which is mediated by its interaction with TCTP.

TCTP is known as having a function in tumor pathogenesis. However, the inventors have surprisingly found that TCTP overexpression in castration sensitive confers castration- and chemo-resistance to the cells.

Furthermore, the inventors have identified antisense oligonucleotides (ASOs) and short interfering RNAs (siRNAs) that significantly decrease TCTP mRNA and protein levels. Moreover, it was demonstrated that the ASO enhanced the anticancer effects of hormono- and chemo-therapy by docetaxel both in vitro and in vivo.

The inventors have thus found that ASOs and siRNAs targeting TCTP restore hormone- and chemo-sensitivity in CRPC. More specifically, the anticancer activity of TCTP siRNAs and ASOs in prostate cancer cells is of great interest for the use of these compounds as therapeutic agents since they are expected not to exhibit toxicity as a side effect. Indeed, TCTP is strongly overexpressed in 75% of advanced stage prostate cancer, in particular in CRPC primary tumors and metastasis. On the other hand, no TCTP expression has been observed in normal prostate tissues. Even normal prostate cancer glands that are found between tumoral prostate cancer glands have no expression of TCTP.

One strategy to improve therapies in advanced prostate cancer involves targeting genes that are activated by androgen withdrawal, either to delay or to prevent the emergence of the CR phenotype. ASOs and siRNAs targeting TCTP are believed to have this capacity. In particular, inhibition of TCTP is believed to be capable of restoring sensibility of cancerous cells that has become resistant to therapies such as chemotherapy and/or castration.

Therefore, the present invention provides several antagonists of Translationally-Controlled Tumor Protein (TCTP), in particular several nucleic acids targeting the mRNA encoding TCTP and that is capable of reducing the amount of TCTP in cancerous cells, for use in the treatment or prevention of cancers preferably castration- or chemo-resistant cancer such as e.g. CRPC or for sensitizing a patient having a castration- or chemo-resistant cancer to therapy.

Antagonists for Use According to the Invention

As used herein, the term "TCTP antagonist" refers to compounds that inhibits or reduces TCTP biological activity. The biological activity of TCTP depends on the amount of the protein (i.e. its expression level) as well as on the activity of the protein. Therefore, the TCTP antagonist may reduce or inhibit either TCTP expression, or TCTP protein activity.

As used herein, the terms "Translationally-Controlled Tumor Protein" and "TCTP" encompass any naturally occurring isoform of the TCTP protein, including the protein of SEQ ID NO: 1, allelic variants thereof, splice variants thereof and homologous proteins in other species. Preferably, TCTP is of human origin. Most preferably, TCTP has the sequence of SEQ ID NO: 1.

Methods for determining whether a compound is a TCTP antagonist are well-known by the skilled in the art.

For example, the skilled in the art can assess whether a compound reduces or abolishes TCTP expression by Western Blotting or by RT-PCR, Elisa (enzyme-linked immunosorbent assay), or immunohistochemistry.

The biological activity of the TCTP protein can also be assessed through measuring one of the phenomenon in which TCTP is known to play a role. For instance, TCTP is known to play a role in histamine release, in the cell cycle, in cellular growth, in apoptosis, in microtubule stabilization, in calcium metabolism, etc. A compound reducing or abolishing the capacity of TCTP to play a role in one of these phenomena is defined as a TCTP antagonist.

For example, determining whether a compound is a TCTP antagonist can be done by measuring the capacity of TCTP to cause histamine release from basophils, e.g. using the method described in MacDonald et al. (1995, Science. 269:688-90), in the presence and in the absence of a candidate compound. A compound reducing or abolishing histamine release is defined as a TCTP antagonist.

The inventors have found that TCTP is a binding partner of Hsp27. The binding of Hsp27 with TCTP protects TCTP from its ubiquitin-proteasome pathway, and inhibition of that interaction leads to TCTP protein degradation (data not published). Thus, the biological activity of TCTP may also be measured by assessing the capacity of TCTP to bind to its natural binding partners such as e.g. Hsp27. The binding of TCTP to Hsp27 may for example be assessed using a co-immunoprecipitation assay, a pull-down assay, a bioluminescence resonance energy transfer (BRET) system or the yeast two-hybrid system (Y2H). A compound reducing or abolishing binding of TCTP to Hsp27 is defined as a TCTP antagonist.

The TCTP antagonist may correspond to any type of molecule, such as e.g. a nucleic acid selected from the group consisting of a nucleic acid targeting TCTP mRNA (e.g. an interfering RNA or an antisense oligonucleotide), a chemical molecule (e.g. a small molecule), a peptide, an aptamer, an antibody or a dominant negative mutant of TCTP or a fragment thereof.

In a preferred embodiment, the TCTP antagonist for use according to invention is a chemical molecule such as an antihistaminic agent.

In a preferred embodiment, the antagonist for use according to invention is a nucleic acid according to the invention as described in detail in the paragraph below.

In another embodiment, the antagonist for use according to invention is a chemical molecule (preferably a small molecule) that specifically binds to the TCTP protein. The antagonist for use according to invention may also be an antibody that specifically binds to the TCTP protein.

As used herein, the terms "Heat Shock Protein 27" and "Hsp27" encompass any naturally occurring isoform of the Hsp27 protein, including the protein of SEQ ID NO: 16, allelic variants thereof, splice variants thereof and homologous proteins in other species. Preferably, Hsp27 is of human origin. Most preferably, Hsp27 is the human heat shock 27 kDa protein 1 (Accession Number AAH12292) and has the sequence of SEQ ID NO: 16.

"Antibody" is meant to include not only whole immunoglobulin molecules but also fragments thereof such as Fab, F(ab')2, Fv and other fragments thereof that retain the antigen-binding site. The term "antibody" also includes genetically engineered derivatives of antibodies such as single chain Fv molecules (scFv) and single domain antibodies (dAbs). The term further includes antibody-like molecules, which may be produced using phage-display techniques or other random selection techniques for molecules. The term includes all classes of antibodies and more specifically IgGs, IgAs, IgMs, IgDs and IgEs.

Although the antibody may be a polyclonal antibody, it is preferred if it is a monoclonal antibody. A "monoclonal antibody" refers to an antibody that recognizes only one type of antigen. The term "monoclonal antibody" encompasses both antibodies produced by hybridomas (Kohler and Milstein 1975 Nature 256:495-7) and recombinant antibodies obtained through genetic engineering. More specifically, monoclonal antibodies encompass chimeric antibodies (Boulianne et al. 1984 Nature 312:643-6), humanized antibodies (Jones et al. 1986 Nature 321:522-5) and fully human antibodies which may be produced e.g. by phage display (Vaughan et al. 1998 Nat Biotechnol. 16:535-9) or transgenic technology (Lonberg 2005 Nat Biotechnol. 23:1117-25).

"Antibody fragments" comprise a portion of an intact antibody, preferably the antigen binding or variable region of the intact antibody. Examples of antibody fragments include Fv, Fab, F(ab')2, Fab', dsFv, scFv, sc(Fv)2, diabodies and multispecific antibodies formed from antibody fragments. The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, preferably by using gene recombination techniques.

"dsFv" is a VH::VL heterodimer stabilised by a disulphide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

In still another embodiment, the antagonist for use according to invention is an aptamer that specifically binds to the TCTP protein.

The term "aptamer," used herein interchangeably with the term "nucleic acid ligand," means a nucleic acid that, through its ability to adopt a specific three dimensional conformation, binds to and has an antagonizing (i.e., inhibitory) effect on a proteic target. The target of the present invention is TCTP and hence the term TCTP aptamer is used. Inhibition of the target by the aptamer may occur by binding of the target, by catalytically altering the target, by reacting with the target in a way which modifies/alters the target or the functional activity of the target, by covalently attaching to the target as in a suicide inhibitor, by facilitating the reaction between the target and another molecule. Aptamers may be comprised of multiple ribonucleotide units, deoxyribonucleotide units, or a mixture of both types of nucleotide residues. Aptamers may further comprise one or more modified bases, sugars or phosphate backbone units as described in further detail herein.

Preferably, the TCTP antagonist is capable of "specifically binding" to TCTP. Methods for determining whether an antibody, an aptamer or a chemical molecule is capable of specifically binding to TCTP are well-known to the skilled in the art. Such methods for example include dose response assays with a competitive ligand, co-immunoprecipitation, surface plasmon resonance (e.g. using a BIA-Core) and yeast two-hybrid assays. Herein, the term "specific binding" to a protein has its usual meaning in the art, and is used to qualify a binding as opposed to a "non-specific binding".

According to the invention, the TCTP antagonist may be a molecule, such as an antibody or aptamer, interfering with TCTP binding to Hsp27. By "interfering with TCTP binding to Hsp27" is meant that the molecule prevents, abolishes, inhibits or reduces binding of TCTP to Hsp27. The inventors have found that TCTP interacts with a C-terminal domain of Hsp27 presumably with the flexible domain (IXI box) of Hsp27 present at the amino acids positions 167 to 179 of Hsp27 (a reference sequence of Hsp27 is shown as SEQ ID NO: 16). Indeed, TCTP binds with a truncated form of HSp27 consisting of amino acids 93 to 205 but does not bind to another truncated form of Hsp27 consisting of amino acids 1 to 173.

The capacity of a candidate molecule to interfere with TCTP binding to Hsp27 may be assayed by any method known to the skilled person, such as immunoprecipitation assays, BRET system, surface plasmon resonance methods, etc. To that end, binding of TCTP to Hsp27 (wild-type or a truncated form of Hsp27 which retains binding capacity to TCTP such as the truncated form of Hsp27 consisting of amino acids at position 93-205 or a polypeptide sequence comprising at least amino acids 167 to 205, preferably, 167 to 179 of Hsp27) may be assayed in the presence and in the absence of the candidate molecule. Decreased binding of TCTP to Hsp27 in the presence of the candidate molecule would be indicative of a TCTP antagonist interfering with TCTP binding to Hsp27.

Nucleic Acids According to the Invention

In a preferred embodiment according to the invention, the TCTP antagonist is a nucleic acid that targets an mRNA encoding Translationally-Controlled Tumor Protein (TCTP), and that is capable of reducing the amount of TCTP in cells.

The present invention provides such nucleic acids that target an mRNA encoding Translationally-Controlled Tumor Protein (TCTP), and that are capable of reducing the amount of TCTP in cells.

As used herein, a nucleic acid that "targets" an mRNA refers to a nucleic acid that is capable of specifically binding to said mRNA. That is to say, the nucleic acid comprises a sequence that is at least partially complementary, preferably perfectly complementary, to a region of the sequence of said mRNA, said complementarity being sufficient to yield specific binding under intra-cellular conditions.

As immediately apparent to the skilled in the art, by a sequence that is "perfectly complementary to" a second sequence is meant the reverse complement counterpart of the second sequence, either under the form of a DNA molecule or under the form of a RNA molecule. A sequence is "partially complementary to" a second sequence if there are one or more mismatches.

Nucleic acids that target an mRNA encoding TCTP may be specific to TCTP and designed by using the sequence of said mRNA as a basis, e.g. using bioinformatic tools. For example, the sequence of SEQ ID NO: 5 can be used as a basis for designing nucleic acids that target an mRNA encoding TCTP.

The nucleic acids according to the invention are capable of reducing the amount of TCTP in cells, e.g. in cancerous cells such as LNCaP, C4-2 or PC3 cells. Methods for determining whether a nucleic acid is capable of reducing the amount of TCTP in cells are known to the skilled in the art. This may for example be done by analyzing TCTP protein expression by Western blot, and by comparing TCTP protein expression in the presence and in the absence of the nucleic acid to be tested (see FIG. 4 and Example 5).

The nucleic acids according to the invention may for example correspond to antisense oligonucleotides or to interfering RNAs (including siRNAs, shRNAs, miRNAs, dsRNAs, and other RNA species that can be cleaved in vivo to form siRNAs).

The nucleic acids according to the invention typically have a length of from 12 to 50 nucleotides, e.g. 12 to 35 nucleotides, from 12 to 30, from 12 to 25, from 12 to 22, from 15 to 35, from 15 to 30, from 15 to 25, from 15 to 22, from 18 to 22, or about 19, 20 or 21 nucleotides.

The nucleic acids according to the invention may for example comprise or consist of 12 to 50 consecutive nucleotides, e.g. 12 to 35, from 12 to 30, from 12 to 25, from 12 to 22, from 15 to 35, from 15 to 30, from 15 to 25, from 15 to 22, from 18 to 22, or about 19, 20 or 21 consecutive nucleotides of a sequence complementary to the mRNA that binds specifically with SEQ ID NO: 5.

In particular, the inventors have identified thirteen nucleic acids targeting an mRNA encoding TCTP that are very efficient in reducing the amount of TCTP in cells (see FIG. 4 and Example 5). These nucleic acids target the regions consisting of nucleotides 153 to 173 of SEQ ID NO: 5, nucleotides 220 to 240 of SEQ ID NO: 5, nucleotides 300 to 320 of SEQ ID NO: 5, and nucleotides 320 to 340 of SEQ ID NO: 5, respectively. All of these nucleic acids target the translated region of the TCTP mRNA (which extends from nucleotide 94 to 612 of SEQ ID NO: 5).

Therefore, the nucleic acids according to the invention preferably target a sequence overlapping with nucleotides 153 to 173, or with nucleotides 221 to 240 or with nucleotides 300 to 340 of SEQ ID NO: 5, said nucleic acid being a DNA or a RNA. Such a nucleic acid may for example target:

a sequence consisting of nucleotides 153 to 173 or of nucleotides 221 to 240 or of nucleotides 300 to 320, or of nucleotides 320 to 340 of SEQ ID NO: 5, or a sequence comprised within nucleotides 153 to 173 or within nucleotides 221 to 240, or within nucleotides 300 to 320, or within nucleotides 320 to 340 of SEQ ID NO: 5, or a sequence partially comprised within nucleotides 153 to 173 or within nucleotides 221 to 240, or within nucleotides 300 to 320, or within nucleotides 320 to 340 of SEQ ID NO: 5

The nucleic acids according to the invention may for example comprise a fragment of at least 10 consecutive nucleotides of a sequence selected from the group consisting of SEQ ID NO: 2 (5'-ACCAATGAGCGAGTCATCAA-3'), SEQ ID NO: 3 (5'-AACCCGUCCGCGAUCUCCCGG-3'), SEQ ID NO: 14 (5'-AACTTGTTTCCTGCAGGTGA-3'), SEQ ID NO: 15 (5'-TGGTTCATGACAATATCGAC-3'), SEQ ID NO: 17 (5'-TAATCATGATGGCGACTGAA-3'), SEQ ID NO: 25 (5'-ACCAGTGATTACTGTGCTTT-3'), SEQ ID NO: 26 (5'-CTTGTAGGCTTCTTTTGTGA-3'), SEQ ID NO: 27 (5'-ATGTAATCTTTGATGTACTT-3'), SEQ ID NO: 28 (5'-GTTTCCCTTTGATTGATTTC-3'), SEQ ID NO: 29 (5'-TTCTGGTCTCTGTTCTTCAA-3'), SEQ ID NO: 34 (5'-AGAAAATCATATATGGGGTC-3'), SEQ ID NO: 36 (5'-TTAACATTTCTCCATTTCTA-3'), SEQ ID NO: 38 (5'-GTCATAAAAGGTTTTACTCT-3') and SEQ ID NO: 40 (5'-GAAATTAGCAAGGATGTGCT-3'). More preferably, the nucleic acids comprise a sequence selected from the group consisting of SEQ ID NO: 2, SEQ ID NO: 3, SEQ ID NO: 14, SEQ ID NO: 15, SEQ ID NO: 17, SEQ ID NO: 25, SEQ ID NO: 26, SEQ ID NO: 27, SEQ ID NO: 28, SEQ ID NO: 29, SEQ ID NO: 34, SEQ ID NO: 36, SEQ ID NO: 38 and SEQ ID NO: 40. The nucleic acids according to the invention may for example comprise a fragment of at least 10 consecutive nucleotides of a sequence of SEQ ID NO: 2 or of a sequence of SEQ ID NO: 14, or of a sequence of SEQ ID NO: 15, or of a sequence of SEQ ID NO: 3. Most preferably, they comprise a sequence of SEQ ID NO: 2, or a sequence of SEQ ID NO: 14, or a sequence of SEQ ID NO: 15 or a sequence of SEQ ID NO: 3.

In a preferred embodiment according to the invention, the nucleic acid is an antisense oligonucleotide. The antisense molecule may be a DNA or a RNA molecule.

Said antisense oligonucleotide may for example comprise or consist of a fragment of at least 10, 12, 15, 18 or 20 consecutive nucleotides of a sequence selected from the group consisting of SEQ ID NO: 2 (5'-ACCAATGAGC-GAGTCATCAA-3'), SEQ ID NO: 14 (5'-AACTTGTTTC-CTGCAGGTGA-3'), SEQ ID NO: 15 (5'-TGGTTCAT-GACAATATCGAC-3'), SEQ ID NO: 17 (5'-TAATCATGATGGCGACTGAA-3'), SEQ ID NO: 25 (5'-ACCAGTGATTACTGTGCTTT-3'), SEQ ID NO: 26 (5'-CTTGTAGGCTTCTTTTGTGA-3'), SEQ ID NO: 27 (5'-ATGTAATCTTTGATGTACTT-3'), SEQ ID NO: 28 (5'-GTTTCCCTTTGATTGATTTC-3'), SEQ ID NO: 29 (5'-TTCTGGTCTCTGTTCTTCAA-3'), SEQ ID NO: 34 (5'-AGAAAATCATATATGGGGTC-3'), SEQ ID NO: 36 (5'-TTAACATTTCTCCATTTCTA-3'), SEQ ID NO: 38 (5'-GTCATAAAAGGTTTTACTCT-3') and SEQ ID NO: 40 (5'-GAAATTAGCAAGGATGTGCT-3'), preferably of a sequence SEQ ID NO: 2 (5'-ACCAATGAGCGAGTCAT-CAA-3'), or of a sequence of SEQ ID NO: 14 (5'-AACTT-GTTTCCTGCAGGTGA-3'), or of a sequence of SEQ ID NO: 15 (5'-TGGTTCATGACAATATCGAC-3'). Preferably, it comprises or consists of a sequence comprises in the group selected of SEQ ID NO: 2, SEQ ID NO: 14, SEQ ID NO: 15, SEQ ID NO: 17, SEQ ID NO: 25, SEQ ID NO: 26, SEQ ID NO: 27, SEQ ID NO: 28, SEQ ID NO: 29, SEQ ID NO: 34, SEQ ID NO: 36, SEQ ID NO: 38 and SEQ ID NO: 40, more preferably, in the group consisting of SEQ ID NO: 2, SEQ ID NO: 14 and SEQ ID NO: 15.

In another preferred embodiment according to the invention, the nucleic acid is an interfering RNA (iRNA).

RNA interference is a term initially coined by Fire and co-workers to describe the observation that double-stranded RNA (dsRNA) can block gene expression when it is introduced into worms (Fire et al., 1998, Nature 391:806-811). dsRNA directs gene-specific, post-transcriptional silencing in many organisms, including vertebrates, and has provided a new tool for studying gene function. RNA interference involves mRNA degradation, but many of the biochemical mechanisms underlying this interference are unknown. The use of RNA interference has been further described in Carthew et al. (2001, Current Opinions in Cell Biology, 13:244-248) and in Elbashir et al. (2001, Nature, 411:494-498). The iRNA molecules of the invention are double-stranded or single-stranded RNA, preferably of from about 21 to about 23 nucleotides, which mediate RNA inhibition. That is, the iRNA of the present invention mediate degradation of mRNA encoding TCTP.

The term "iRNA" include double-stranded RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the iRNA molecules of the present invention can also comprise non-standard nucleotides, including non-naturally occurring nucleotides or deoxyribonucleotides. Collectively, all such altered iRNA compounds are referred to as analogs or analogs of naturally-occurring RNA. iRNA of the present invention need only be sufficiently similar to natural RNA that it has the ability to mediate RNA interference. As used herein the phrase "mediate RNA Interference" refers to and indicates the ability to distinguish which mRNA are to be affected by the RNA interference machinery or process. RNA that mediates RNA interference interacts with the RNA interference machinery such that it directs the machinery to degrade particular mRNAs or to otherwise reduce the expression of the target protein. In one embodiment, the present invention relates to iRNA molecules that direct cleavage of specific mRNA to which their sequence corresponds. It is not necessary that there be perfect correspondence of the sequences, but the correspondence must be sufficient to enable the iRNA to direct RNA interference inhibition by cleavage or lack of expression of the target mRNA.

The iRNA molecules of the present invention may comprise an RNA portion and some additional portion, for example a deoxyribonucleotide portion. The total number of nucleotides in the RNA molecule is suitably less than 49 in order to be effective mediators of RNA interference. In preferred RNA molecules, the number of nucleotides is 16 to 29, more preferably 18 to 23, and most preferably 21-23.

As indicated above, the term "iRNA" includes but is not limited to siRNAs, shRNAs, miRNAs, dsRNAs, and other RNA species that can be cleaved in vivo to form siRNAs.

A "short interfering RNA" or "siRNA" comprises a RNA duplex (double-stranded region) and can further comprises one or two single-stranded overhangs, 3' or 5' overhangs.

A "short hairpin RNA (shRNA)" refers to a segment of RNA that is complementary to a portion of a target gene (complementary to one or more transcripts of a target gene), and has a stem-loop (hairpin) structure.

"MicroRNAs" or "miRNAs" are endogenously encoded RNAs that are about 22-nucleotide-long, that post-transcriptionally regulate target genes and are generally expressed in a highly tissue-specific or developmental-stage-specific fashion. One can design and express artificial miRNAs based on the features of existing miRNA genes. The miR-30 (microRNA 30) architecture can be used to express miRNAs (or siRNAs) from RNA polymerase II promoter-based expression plasmids (Zeng et al, 2005, Methods enzymol. 392:371-380). In some instances the precursor miRNA molecules may include more than one stem-loop structure. The multiple stem-loop structures may be linked to one another through a linker, such as, for example, a nucleic acid linker, a miRNA flanking sequence, other molecules, or some combination thereof.

In a preferred embodiment according to the invention, the iRNA comprise or consist of a fragment of at least 10, 12, 15, 18 or 20 consecutive nucleotides of a sequence of SEQ ID NO: 3 (5'-AACCCGUCCGCGAUCUCCGG-3'). Preferably, such a nucleic acid is an iRNA comprising or consisting of a sequence of SEQ ID NO: 3. Most preferably, such a nucleic acid is a siRNA or a shRNA. The sequence of SEQ ID NO: 3 may be modified, and e.g. correspond to a modified sequence of SEQ ID NO: 3 such as a 5'-AAC-CCGUCCGCGAUCUCCGdGdG-3' sequence.

The nucleic acids employed as antisense or iRNA molecules may be modified, preferably chemically modified, in order to increase the stability and/or therapeutic efficiency of the nucleic acids in vivo.

For example, the oligonucleotides may be employed as phosphorothioate derivatives (replacement of a non-bridging phosphoryl oxygen atom with a sulfur atom) which have increased resistance to nuclease digestion. MOE modification (ISIS backbone) or lipid-modified (Philippe Barthelemy's Backbone) are also effective.

Additionally or alternatively, some nucleobases of an iRNA molecule may be present as desoxyriboses. That modification should only affect the skeleton of the nucleobase, in which the hydroxyle group is absent, but not the side chain of the nucleobase, which remains unchanged. Such a modification usually favors recognition of the iRNA by the DICER complex.

Therapeutic Uses of the Antagonists According to the Invention

The inventors have found that the siRNAs and antisense oligonucleotides targeting TCTP inhibit the castration-resistant progression of PC3, LNCaP and C4-2 cells and xenografts and enhance docetaxel and castration-sensitivity. Therefore, the present invention provides a TCTP antagonist, e.g. a nucleic acid according to the invention as defined hereabove, for use in the treatment or prevention of cancer preferably hormone- and/or chemo-resistant cancer. The present invention also provides a TCTP antagonist for use in restoring sensibility to hormone- and/or chemo-therapy in a patient suffering from cancer.

The invention also provides a method for treating or preventing cancer and/or for restoring sensibility to hormone- and chemo-therapy comprising the step of administering an effective amount of an antagonist according to the invention to an individual in need thereof.

As used herein, the term "cancer" refers to any type of malignant (i.e. non benign) tumor. The tumor may correspond to a solid malignant tumor, which includes e.g. carcinomas, adenocarcinomas, sarcomas, malignant melanomas, mesotheliomas, blastomas, or to a blood cancer such as leukaemias, lymphomas and myelomas. The cancer may for example correspond to an advanced prostate cancer, a pancreatic cancer, a bladder cancer, an ovarian cancer, a testicular cancer, a cortical adenoma, a colon cancer, a colorectal cancer, a breast cancer or a liver cancer.

Cancers which are preferably treated according to the invention are those wherein TCTP is expressed at higher levels in cancerous cells than in non-cancerous cells of the same tissue type. Exemplary such cancers include without limitation prostate cancer, colon cancer, colorectal cancer, breast cancer, liver cancer, erythroleukemia, gliomas, melanomas, hepatoblastomas and lymphomas.

The antagonists according to the invention are believed to be capable of delaying or preventing the emergence of a resistant hormone-independent phenotype, and to be capable of reversing a resistant hormone-independent phenotype. They are thus particularly suitable for use in the treatment of a hormone-independent cancer or of a hormone-dependent cancer in which hormone-independency is expected to occur. The term "castration" in the expression "castration-resistant" or "castration-independency" according to the invention refers to "hormone" and corresponds to "Hormone-resistant" or "hormone-independency". Androgen independency refers to a hormone-independency. Indeed, an androgen-independent prostate cancer (AIPC) is a castration-resistant prostate cancer (CRPC)

Therefore, a preferred embodiment is directed to an antagonist according to the invention for use in the treatment or prevention of a hormone-independent or chemo-resistant cancer Since the antagonists according to the invention are capable of restoring sensitivity to drugs, they are particularly suitable for use in the treatment of advanced cancers or chemotherapy resistant cancers. The antagonists according to the invention can notably be used as a second line therapy.

The skilled in the art is capable of determining whether a cancer is an "advanced" cancer using well-known classification methods, such as e.g. the grade or the TNM classification. For example, the grade (G1-4) of the cancer cells may be used. More specifically, cancer cells are "low grade" if they appear similar to normal cells, and "high grade" if they appear poorly differentiated. For example, a G3 or G4 cancers would be classified as advanced cancers. Additionally or alternatively, the TNM classification may be used. In this classification, T(a,is,(0),1-4) indicates the size or direct extent of the primary tumor, N(0-3) indicates the degree of spread to regional lymph nodes, and M(0/1) indicates the presence of metastasis. For example, a T4/N3/M1 cancer would be classified as an advanced cancer.

Most preferably, the cancer is a prostate cancer, e.g. an advanced prostate cancer and/or an androgen-independent prostate cancer. In a specific embodiment, androgen-dependent prostate cancers can be excluded from the scope of the cancers to be treated in the frame of the present invention.

The inventors have further found that the antisense oligonucleotides according to the invention enhanced the anti-cancer effects of chemotherapy by docetaxel both in vitro and in vivo. In particular, the antagonists according to the invention are believed to be capable of reversing a castration-resistant phenotype and of restoring sensitivity to drugs. Therefore, the antagonist in accordance with the invention can advantageously be used (simultaneously or sequentially) in combination with at least one second anti-cancer agent (e.g. in the frame of a chemotherapy).

In particular, the antagonist according to the invention may be used in the frame of a combination chemotherapy. The antagonist according to the invention may for example be used (simultaneously or sequentially) in combination with at least one of the following anti-cancer agents:

an antimitotic agent such as Docetaxel, Vincristine, Paclitaxel (Taxol), Vinorelbine, and Abraxane;

a hormonal therapy drug, such drugs being commonly used in the frame of treatment of hormone-sensitive cancers. Hormonal therapy drugs include, e.g., Tamoxifen, Gonadotrophin-releasing hormone (GnRH) agonists and antagonists, androgen receptor (AR) antagonist, and estrogen receptor (ER) antagonists;

an alkylating agent such as Cyclophosphamide, Chlorambucil and Melphalan;

an antimetabolite such as Methotrexate, Cytarabine, Fludarabine, 6-Mercaptopurine and 5-Fluorouracil;

a topoisomerase inhibitor such as Doxorubicin, Irinotecan, Platinum derivatives, Cisplatin, Carboplatin, Oxaliplatin;

an aromatase inhibitor such as Bicalutamide, Anastrozole, Examestane and Letrozole;

a signaling inhibitor such as Imatinib (Gleevec), Gefitinib and Erlotinib;

a monoclonal antibody such as Rituximab, Trastuzumab (Herceptin) and Gemtuzumab ozogamicin;

a biologic response modifier such as Interferon-alpha;

a differentiating agent such as Tretinoin and Arsenic trioxide; and/or an agent that block blood vessel formation (antiangiogenic agents) such as Bevicizumab, Serafinib and Sunitinib.

In addition, the method of treating or preventing cancer according to the invention may be associated with a radiation therapy, surgery and/or androgen withdrawal.

Administration of antagonists according to the invention, and in particular of antisense oligonucleotides and of iRNAs, can be carried out using various mechanisms known in the art, including naked administration and administration in pharmaceutically acceptable lipid carriers or nanoparticles. For example, lipid carriers for antisense delivery are disclosed in U.S. Pat. Nos. 5,855,911 and 5,417,978.

They may be for example administered by intravenous, intraperitoneal, subcutaneous or oral routes, or direct local tumor injection.

The antagonist is administered in an "effective amount", i.e. in an amount sufficient to treat or prevent the cancer. It will be appreciated that this amount will vary both with the effectiveness of the antisense oligonucleotides or other therapeutic agent employed, and with the nature of any carrier used. The determination of appropriate amounts for any given composition is within the skill in the art, through standard series of tests designed to assess appropriate therapeutic levels.

In the frame of the present invention, the individual preferably is a human individual. However, the veterinary use of the antagonist according to the present invention is also envisioned. The individual may thus also correspond to a non-human individual, preferably a non-human mammal.

The term "treating" is meant a therapeutic method, i.e. a method aiming at curing, improving the condition and/or extending the lifespan of an individual suffering from the cancer.

By "preventing" is meant a prophylactic method, e.g. aiming at reducing the risk of relapse and/or reducing the risk of appearance of a hormone-independency.

Prostate cancer is one cancer that overexpresses TCTP in advanced cancers, and in particular in cancers that have become castration-resistant. For treatment of prostate cancer, the antagonists of the invention are suitably administered after initial of androgen withdrawal. Initiation of androgen withdrawal may be accomplished via surgical (removal of both testicles) or medical (drug-induced suppression of testosterone) castration, which is currently indicated for treatment of prostate cancer. Medical castration can be achieved by various regimens, including LHRH agents or antiandrogens (see e.g. Cleave et al., 1999, CMAJ 160:225-232). Intermittent therapy in which reversible androgen withdrawal can be performed as described in Cleave et al. (1998, Eur. Urol. 34: 37-41).

The inhibition of TCTP, in particular of TCTP expression by the nucleic acids according to the invention, may be transient. For treatment of prostate cancer, the TCTP inhibition should ideally occur coincident with androgen withdrawal. In humans, this means that TCTP inhibition should be effective starting within a day or two of androgen withdrawal (before or after) and extending for about 3 to 6 months. This may require multiple doses to accomplish. It will be appreciated, however, that the period of time may be more prolonged, starting before castration and expending for substantial time afterwards without departing from the scope of the invention.

Pharmaceutical Compositions According to the Invention

The present invention also provides a pharmaceutical composition comprising an antagonist according to the invention, in particular a nucleic acid according to the invention as defined in the above paragraph, and a pharmaceutically acceptable carrier, as well as such an antagonist according to the invention for use as a medicament.

Pharmaceutical compositions formulated in a manner suitable for administration of nucleic acids are known to the skilled in the art. For example, lipidic carriers (in particular liposomes) are particularly suitable pharmaceutically acceptable carriers when administering a nucleic acid according to the invention.

Non-limiting examples of pharmaceutically acceptable carriers suitable for formulation with the nucleic acid of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, biodegradable polymers (such as poly(DL-lactide-coglycolide) microspheres) for sustained release delivery after implantation, and loaded nanoparticles (such as those made of polybutylcyanoacrylate).

The invention also features pharmaceutical composition comprising surface-modified liposomes containing poly (ethylene glycol) lipids (PEG-modified, branched and unbranched or combinations thereof, or long-circulating liposomes or stealth liposomes). Nucleic acids of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al., 1995, Chem. Rev., 95:2601-2627; lshiwata et al., 1995, Chem. Pharm. Bull., 43:1005-1011). Such liposomes have been shown to accumulate selectively in tumors, presumably by extravasation and capture in the neovascularized target tissues (Lasic et al., 1995, Science, 267:1275-1276; Oku et al., 1995, Biochim. Biophys. Acta, 1238:86-90). The long-circulating liposomes enhance the pharmacokinetics and pharmacodynamics of DNA and RNA. Long-circulating liposomes are also likely to protect drugs from nuclease degradation to a greater extent compared to cationic liposomes.

The pharmaceutical composition of the invention may comprise stabilizers, buffers, and the like. When it is desired to use a liposome delivery mechanism, standard protocols for formation of liposomes can be followed. The compositions of the present invention may be formulated and used as tablets, capsules or elixirs for oral administration, suppositories for rectal administration, sterile solutions or suspensions for injectable administration.

The choice of the formulation ultimately depends on the intended way of administration, such as e.g. an intravenous, intraperitoneal, subcutaneous or oral way of administration, or a local administration via tumor injection. Preferably, the pharmaceutical composition according to the invention is a solution or suspension, e.g. an injectable solution or suspension. It may for example be packaged in dosage unit form.

All references cited herein, including journal articles or abstracts, published patent applications, issued patents or any other references, are entirely incorporated by reference herein, including all data, tables, figures and text presented in the cited references.

Although having distinct meanings, the terms "comprising", "having", "containing" and "consisting of" may be replaced with one another throughout the above description of the invention.

In the frame of the present description, all compounds, polypeptides and peptides may optionally be isolated and/or purified.

The invention will be further evaluated in view of the following examples and figures.

BRIEF DESCRIPTION OF THE SEQUENCES

Figure 1:
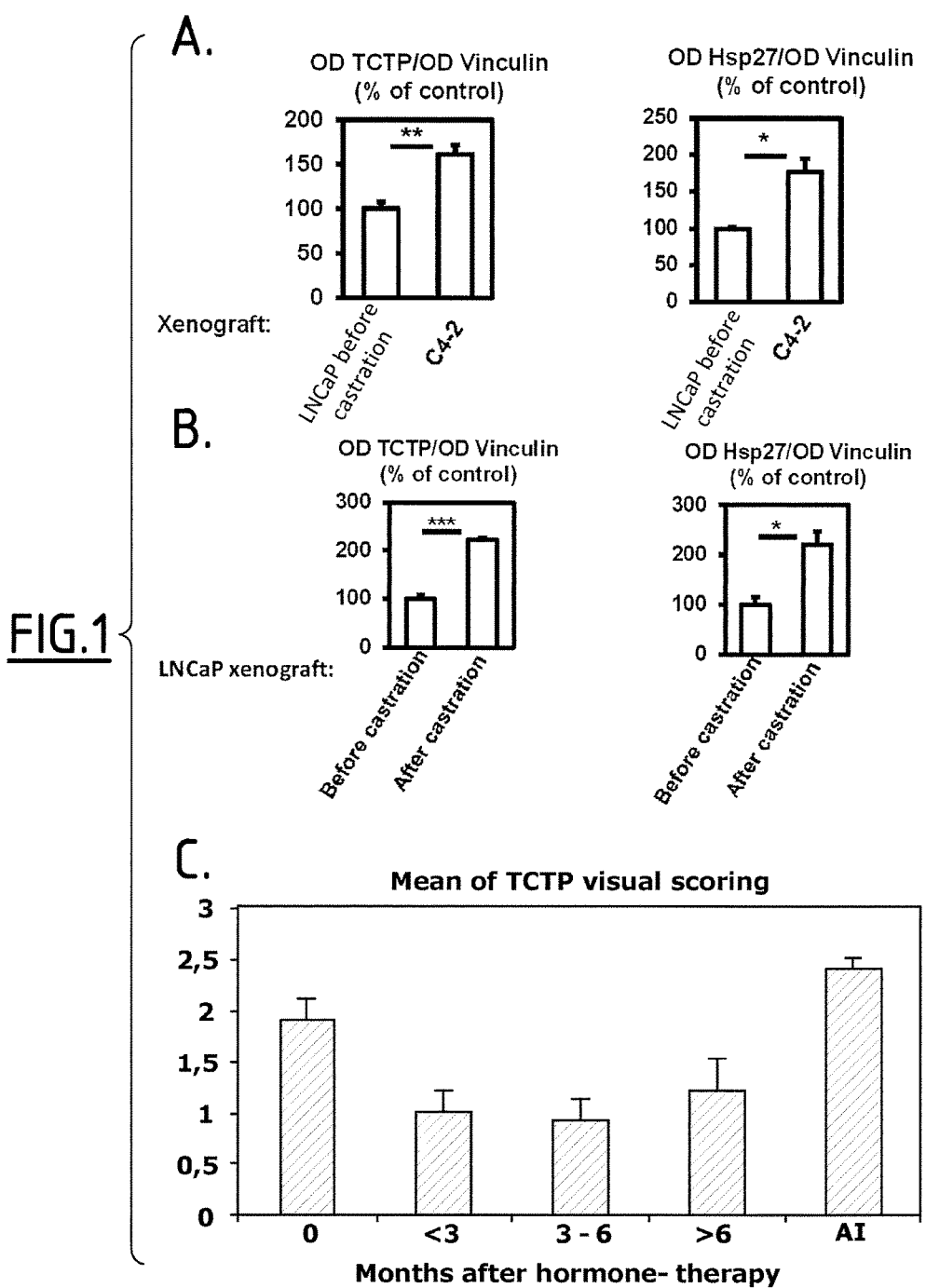
FIG. 1 illustrates TCTP expression level after androgen withdrawal.

SEQ ID NO: 1 shows the sequence of human TCTP protein.

SEQ ID NO: 2, SEQ ID NO: 14, SEQ ID NO: 15 and SEQ ID NO: 17 to SEQ ID NO: 40 show ASO sequences; sequences SEQ ID NO: 2, SEQ ID NO: 14 and SEQ ID NO: 15 being TCTP ASO sequences according to the invention.

SEQ ID NO: 3 shows the sequence of a TCTP siRNA according to the invention.

SEQ ID NO: 4 shows the sequence of a scramble oligonucleotide that has been used as a control.

SEQ ID NO: 5 shows the sequence of a human TCTP mRNA. The regions that are targeted by the TCTP ASO of SEQ ID NO: 2 and by the TCTP siRNA of SEQ ID NO: 3 are indicated.

SEQ ID Nos. 6 to 13 show the sequences of primers used in the Examples.

SEQ ID NO: 16 Hsp27 protein sequence

EXAMPLES

Example 1

Materials and Methods

Nucleic Acids

The known sequence of human TCTP mRNA (Accession number in the NCBI database: NM_003295) served as the basis for the design of antisense oligonucleotide (ASO) and small interference RNA (siRNA) nucleotide inhibitors. Phosphorothioate ASO was obtained by Eurofins MWG Operon (Germany). Preferred ASOs have the sequences 5'-ACCAATGAGCGAGTCATCAA-3' (SEQ ID NO: 2), 5'-AACTTGTTTCCTGCAGGTGA-3' (SEQ ID NO: 14) and 5'-TGGTTCATGACAATATCGAC-3' (SEQ ID NO: 15). A scrambled oligonucleotide 5'-CGTGTAGGTACG-GCAGATC-3' (SEQ ID NO: 4) was used as a control. The sequence of TCTP siRNA was 5'-AACCCGUCCGCGAU-CUCCCdGdG-3' (i.e. a sequence of SEQ ID NO: 3 in which the two C-terminal guanosines are desoxyriboses. This modification only affects the skeleton of the nucleobase, in which the hydroxyle group is absent, but the side chain remains unchanged). This siRNA and its respective validated scrambled siRNA, used as a control for siRNA experiments, were obtained from Qiagen (France).

Cell Lines and Cell Culture Conditions.

The CR prostate cancer cell line PC-3 was purchased from the American Type Culture Collection (Rockville, Md., USA). The cells were maintained in Dulbecco's Modified Eagle's Medium (Invitrogen, Cergy Pontoise, France), supplemented with 10% fetal calf serum (FCS). The human castration sensitive (CS) prostate cancer cell line LNCaP cells were kindly provided by the University of Virginia (Charlottesville, Va., USA), the human CR prostatic cancer cell line C4-2 was made by Dr Martin Gleave (The Prostate Centre, Vancouver, Canada) and the normal prostate cell line PNT2C2 was kindly provided by the York Cancer Research (University of York, York, UK). Those cells were maintained in RPMI 1640 (Invitrogen) supplemented with 10% FCS. Colorectal cancer REG cells were kindly provided by Dr Carmen Garrido (INSERM U-517, Faculty of Medicine and Pharmacy, Dijon, France) and maintained in F10 medium (Invitrogen) supplemented with 10% FCS.

Lentiviral Infection of Hsp27 into LNCaP Cells.

The full-length cDNA for human Hsp27 was sub-cloned into the lentiviral vector pHR'-CMV-EGFP at the BamHI and XhoI sites as described before (Rocchi et al., 2005, Cancer Res, 65: 11083-11093).

Sos Recruitment System (SRS) Yeast Medium

The yeast cells were grown for transformation in YPAD (Yeast Peptone ADenine) medium (1% yeast extract, 2% Bactopeptone, 2% dextrose, 40 mg adenine sulphate, 40% glucose per liter). The selection medium (dropout) consisted of 1.7 g/L of yeast nitrogen base without amino acids, 5 g/L of ammonium sulfate, 20 g/L of dextrose, amino acids, and additional supplements as suggested by the manufacturer (Stratagene, Palo Alto, USA). Galactose medium was prepared by substituting glucose with 20 g/L galactose and 10 g/L raffinose. Solid medium was prepared by adding 1.7% agar prior to autoclaving.

Yeast Two-Hybrid Sos Recruitment System (SRS) Screening.

We used the SRS yeast two-hybrid system from Stratagene (CytoTrap) to identify Hsp27 protein interactors. For this, human Hsp27 was fused to the N-terminal 1070 residues of human Sos and used as bait. We screened a testis plasmid cDNA library and a cervix cancer HeLa cDNA library each constructed in the pMyr vector (Stratagene) with $4.5 \times 10^6$ primary colonies and an average insert size of 1.7 kb according to the manufacturer's instructions. All yeast transformations were performed using the standard lithium acetate method. For the CytoTrap screening, the cdc25H yeast strain was cotransformed with 20 mg of pMyr-cDNA library plasmid and 20 mg of pSos-bait recombinant plasmid. Transformants ($5 \times 10^6$) were screened for each bait protein. Resulting transformants were grown for 3 days at permissive temperature (24° C.) on selection medium containing glucose and additional supplements excluding leucine and uracil (SC-Leu-Ura). After replica plating onto selective minimal galactose plates, colonies that showed growth under restrictive temperature (37° C.) were considered positives clones. Colonies were patched on glucose containing medium and grown at 24° C. for 2 days. They were then replica plated on to glucose and galactose plates and grown at 37° C. Colonies that show growth only on galactose and not on glucose medium were selected and confirmed as true positives by a second round of screening. These clones were grown in liquid medium, yeast cell wall was disrupted by vortexing with glass beads (Sigma) and plasmids were isolated by the Wizard Plus SV Miniprep kit (Promega). 5 µl of the plasmid preparation was used for each PCR reactions using GoTaq (Promega) and pMyr vector specific primers (forward 5'-AACCCCGGATCGGAC-TACTA-3', SEQ ID NO: 6; reverse 5'-AATAAGCTCTA-GAGGGCCGC-3', SEQ ID NO: 7). Presence of a single amplicon was confirmed by agarose gel electrophoresis and sequencing was carried out by the Genome Express sequencing service (http://www.cogenics.com/). Identification of insert sequences was done by database searches using the NCBI BLAST Service (Altschul et al., 1997, Nucleic Acids Res. 25:3389-402).

Western Blot Analysis.

Western Blot analysis was performed as described previously (Rocchi et al., 2004, Cancer Res. 64:6595-602) with 1:5000 rabbit anti-Hsp27 polyclonal antibody (Assay Designs, Villeurbanne, France), 1:2000 rabbit TCTP polyclonal antibody (Abcam Inc., Cambridge, UK), 1:250 rabbit anti-MSL1v1 polyclonal antibody (Abcam Inc.), 1:500 mouse anti-ubiquitin monoclonal antibody (Santa Cruz Biotechnology Inc., Heidelberg, Germany) or 1:1000 rabbit anti-caspase-3 polyclonal antibody (Cell Signalling Technology Inc., Danvers, USA). Loading levels were normalized using 1:5000 rabbit anti-glyceraldehyde-3-phosphate dehydrogenase polyclonal (Abcam Inc.) or 1:2500 mouse anti-vinculine monoclonal antibodies (Sigma Chemical Co., St Louis, Mo., USA).

TMA Construction.

TCTP expression was assessed in 2 different tissue microarray (TMA) from samples before and after castration-therapy (CT) (or Homone-therapy, HT). The first TMA was made in Marseille by S. Giusano with different non treated prostate samples (n=131) included 20, 56, 10 and 5 prostate adenocarcinomas (ADK) with Gleason score 6, 7, 8 and 9 respectively, 16 normal prostate tissues, 6 prostatic intraepithelial neoplasia (PIN) lesions, 12 Benign Prostate Hyperplasia (BPH) and 6 negative controls (placenta). Two cores were punched per Gleason grade (i.e. 2, 4 or 6 cores per patient) with a total of 330 cores. Cores were sampled using a tissue-arrayer (Alphelys, Plaisir, France). Core cylinders of 0.6 mm diameter punched from the donor block were then deposited in the recipient paraffin block. TMA sections (4 µm thick) were cut 24 hours before immunohistochemical processing. The second TMA was made by L. Fazli in Vancouver and included castration-treated (CT) or hormone-treated(HT) prostate tissues (n=232) obtained from the tissue bank in the Department of Pathology and Prostate Research Laboratory in the Jack Bell Research Centre at the Vancouver General Hospital. Most tissues were from radical prostatectomy specimens while CR tissues were obtained from transurethral resections. Specimens were chosen to represent various treatment duration of androgen withdrawal therapy before radical prostatectomy ranging from no treatment (n=35), 0 to 3 months (n=58), 3 to 6 months (n=52), and 6 months (n=57). CR tumors were also identified (n=30). This TMA was constructed using a Beecher microarrayer from radical prostatectomy and transurethral samples (Beecher Instruments, Silver Spring, Md.). Each patient sample was represented with 3 cores in the TMA.

Tissue microarray Analysis.

The first TMA was analyzed as described previously (Charpin et al., 2009, Int J Oncol 34:983-93; Charpin et al., 2009 Int J Cancer 124:2124-34; Garcia et al., 2007, Hum Pathol 38:830-41) with 1:100 anti-TCTP antibody (Abcam). And the second TMA analysis was performed as described previously (Rocchi et al., 2004, Cancer Res. 64:6595-602) with 1:50 anti-TCTP antibody (Abcam).

Image Analysis Procedure.

Image analysis was used for quantification of immunohistochemistry. The first TMA analysis with the SAMBA 2050 automated device (SAMBA Technologie/TRIBVN, Châtillon 92320, France) was performed as previously described (Charpin et al., 1998, J Pathol 184:401-7; Altman et al., 1994, J Natl Cancer Inst 86:829-35; Charpin et al., 2009, Int J Oncol 34:983-93; Charpin et al., 2009 Int J Cancer 124:2124-34; Garcia et al., 2007, Hum Pathol 38:830-41). For the second TMA, photomicrographs were taken through a Leica DMLS microscope coupled to a digital camera (Photometrics CoolSNAP, Roper Scientific, Inc., Glenwood, Ill.) as previously described (Rocchi et al., 2004, Cancer Res. 64:6595-602).

Immunofluorescence.

LNCaP-Mock and -Hsp27 cells were grown on glass coverslips in RPMI media and 10% fetal bovine serum for 24 h. Subsequently, cells were fixed with cold 4% paraformaldehyde for 10 min at 25° C. and permeabilized in 0.05% Triton X-100 in PBS. Slides were incubated in blocking solution of 1% bovine serum albumin in PBS for 30 min and treated with primary antibodies mouse monoclonal Hsp27 (StressGen) and rabbit polyclonal TCTP (Abcam) simultaneously overnight. Secondary fluorescent antibodies goat antimouse Alexa Fluor 546 (Invitrogen) and goat anti-rabbit Alexa Fluor 488 (Invitrogen) were added for 1 hour at room temperature with 35 min washes in PBS. Preparations were mounted with fluorescent 4,6-diamidino-2-phenylindole vectashield mounting media (Vector Laboratories, Clinisciences, Montrouge, France). Images were captured using a Zeiss 510 META fluorescence confocal microscope plan 63X/1.4 (Le Pecq, France) followed by analysis of focal colocalization performed with Image Proplus 6 software (MediaCybernetics, Wokingham, UK) with an assignment of yellow for colocalized foci and green or red as non-colocalization.

Immunoprecipitation

Cleared lysates (250 µg) with adjusted protein concentration (Protein assay, BioRad, Marnes-la-Coquette, France) were used for immunoprecipitation (IP) with 1:50 rabbit anti-TCTP antibody (Abcam) O/N at 4° C. Immune complexes were precipitated after 1 h incubation with 30 ml of TrueBlot anti-rabbit Immunoglobulin beads (eBiosciences, Paris, France). After washing three times in cold lysis buffer, the complexes were resuspended in protein sample buffer (Bio-Rad) and boiled for 5 min before western blot was performed as described before. We used the rabbit True Blot anti-rabbit IgG secondary antibody (Biosciences) to reveal the western blot.

Analysis of TCTP mRNA Expression.

The quantitative reverse transcription polymerase chain reaction (qRT-PCR) analysis was done on a LightCycler detection system (Roche Applied Science, Meylan, France). Expression levels of 18S subunit of the ribosome gene were used as an internal control. First strand cDNA was synthesized from 1 µg of total RNA using random hexamers and expanded by reverse transcriptase according to the manufacturer's instructions (ImProm-II Reverse Transcription System, Promega, Charbonniéres-les-Bains, France), subsequently diluted 1:10 with water, and stored at −20° C. until use. TCTP and 18S polymerase chain reaction (PCR) products were detected by quantitative real time PCR (qRT-PCR) using the SYBR Premix Ex Taq (Takara Bio Inc, St Germain en Laye, France) following the manufacturer's instructions. Five microliters of diluted cDNA template were mixed with 10 µl SYBR Premix Ex Taq (including Taq polymerase, reaction buffer, MgCl2, SYBR green I dye, and deoxynucleotide triphosphate mix) and 0.4 µM forward and reverse primers, in a final volume of 20 µl. The following primers were used: TCTP forward 5'-GAAAGCACAGTAAT-CACTGGTGT-3' (SEQ ID NO: 8) and TCTP reverse 5'-GCAGCCCCTGTCATAAAAGGT-3'; (SEQ ID NO: 9); 18S forward 5'-CTACCACATCCAAGGAAGGC-3' (SEQ ID NO: 10) and 18S reverse 5'-TTTTCGTCACTACCTC-CCCG-3' (SEQ ID NO: 11). After an initial Taq activation for 10 seconds at 95° C., Light Cycler PCR was done using 55 cycles with the following cycling conditions: 95° C. for 5 seconds, 58° C. for 7 seconds, and 72° C. for 14 seconds. Each sample was analyzed in duplicate and the experiment was repeated three times. Results were analyzed using RealQuant data analysis software (Roche, Neuilly-sur-seine, France). The results analysis was done with the 2(-Delta Delta C(T)) Method (Livak K J. et al., 2001; Methods. 25:402-8).

Antisense Oligonucleotides (ASO) and Short-Interfering RNA (siRNA) Sequences.

2'-O-(2-rnethoxyethyl) ASO, OGX-427, was obtained from OncoGenex. The sequence of OGX-427 corresponds to the human Hsp27 translation initiation site (5'-GGGACGCGG-CGCTCGGTCAT-3') (SEQ ID NO: 12). A mismatch ASO (ASO; 5'-CAGCAGCAGAGTATTTAT-CAT-3') (SEQ ID NO: 13) was used as a control. The TCTP phosphorithioate ASO targeting the human TCTP (5'-AC-CAATGAGCGAGTCATCAA-3') (SEQ ID NO: 2) and the control oligonucleotide (5'-CGTGTAGGTACGGCAGATC-3') (SEQ ID NO: 4) were purchased from Operon (Eurofin MWG, Courtaboeuf, France) and designated ASO TCTP or ASO scrambled. The TCTP siRNA (5'-AACCCGUCCGC-GAUCUCCCdGdG-3') (i.e. a sequence of SEQ ID NO: 3 in which the two C-terminal guanosines are desoxyriboses. This modification only affects the skeleton of the nucleobase, in which the hydroxyle group is absent, but the side chain remains unchanged) was validated and purchased from Qiagen (Courtaboeuf, France). The control siRNA was also from Qiagen.

Treatment of Cells with ASO and siRNA.

Cells were plated at a density of 25,000 (PC-3) and 75 000 (LNCaP and C4-2) by 1.9 cm² and treated the day after with indicated siRNA or ASO for 1 or 2 days respectively. Oligofectamine, a cationic lipid (Invitrogen), was used to increase siRNA or ASO uptake into the cells. Cells were treated with indicated siRNA or ASO concentrations after a preincubation for 20 min with 3 mg/ml of oligofectamine in serum free OPTI-MEM (Invitrogen). Four hours later, 1 ml of FCS was added in the medium. To study the effects on rates of TCTP proteasome degradation, cycloheximide (10 µg/ml) and MG132 (10 µmol/1) were added at the end of the second transfection with ASO in replaced medium for 24, 48 and 72 h.

Transient Transfection of TCTP into C4-2 and LNCaP Cells.

Cells were transfected the day after seeding with pcDNA 3.2/V5-DEST vector (Invitrogen) containing TCTP wt (pD-EST-TCTP) or empty control vector (pDEST-control). FuGENE HD Transfection Reagent (Promega) was used to transfect the DNA into the C4-2 and LNCaP cells. The DNA was diluted in serum free OPTI-MEM (Invitrogen) at 0.02 µg/µl and the FuGENE HD reagent was added using the 7:2 ratio. After 30 min of incubation at room temperature, the transfection complex was added to the cells in a drop-wise manner.

In Vitro Mitogenic Assay.

The in vitro effects of Hsp27 and TCTP downregulation notably using siRNA or ASO or TCTP upregulation on apoptosis induced by docetaxel and androgen withdrawal were assessed using the crystal violet assay for LNCaP or C4-2 and bromure de 3-(4,5-dimethylthiazol-2-yl)-2,5-diphenyl tetrazolium (MTT) assay for PC-3 as previously described (Rocchi et al., 2004, Cancer Res. 64:6595-602; Gleave et al., 1999, Clin Cancer Res 5:2891-8). In brief, cells were seeded in each well of 12-well microtiter plates (30 000 to 50 000 cells per well) and allowed to attach overnight. To study the effect of TCTP downregulation on apoptosis induced by docetaxel, PC-3 cells were transiently transfected the day after seeding with 5 nM of TCTP siRNA for 48 h or 100 nM of TCTP ASO for 72 h. Cells were then treated with 50 nM of docetaxel and MTT assays were performed after 24 h. To assess the effect of TCTP downregulation on Hsp27 cytoprotection, LNCaP-Mock and -Hsp27 cells were transiently transfected the day after seeding with 5 nM of TCTP siRNA for 48 h. The down- or upregulation of TCTP effect on LNCaP and C4-2 cell viability was realized after transient transfections with 100 nM of TCTP ASO or 0.02 µg/µl of pDEST-TCTP for 72 h and 48 h respectively. Cells were then treated with 1 nM of docetaxel in serum-free media (mimics androgen withdrawal in vitro) and crystal violet assays were performed the day after. Each assay was performed in triplicate.

Flow Cytometric Analysis.

Flow cytometry of propidium iodide-stained nuclei was performed as described previously (Rocchi et al., 2004, Cancer Res. 64:6595-602). In brief, PC-3 cells were plated at the density of $10^6$ cells into 10 cm dishes in DMEM supplemented with 10% FCS. To assess the effect of TCTP inhibition on apoptosis and cell cycle, cells were treated the day after seeding with 5 nM of siRNA TCTP or control and 100 nM of ASO TCTP or scrambled control for 48 h. Cells were then treated with 50 nM of docetaxel. After 24 h, the cells were analyzed for relative DNA content on a dual laser flow cytometer (FACSCalibur, Becton Dickinson Biosciences, Le Pont de Claix, France). Each assay was performed in triplicate.

Viability Assay by Cell Countess.

PC-3 cells were treated with 70, 100 or 200 nM of TCTP ASO or control. 3 days after, the cells were harvested, combined with 10 µl of trypan blue and counted with Invitrogen Countess. Viability, cell concentration and size were recorded for each sample following the manufacturer's instructions.

Assessment of In Vivo Tumor Growth.

Approximately $3.10^6$ PC-3 cells and $10.10^6$ LNCaP cells were inoculated subcutaneously with 0.1 mL of Dulbecco's Modified Eagle's Medium (Invitrogen) supplemented with 10% FCS for PC-3 or with 0.1 mL of Matrigel (BD Biosciences Discovery Labware) for LNCaP in the flank region of 4-week-old male athymic nude mice (Charles River, L'Arbresle, France) via a 23-gauge needle. When PC-3 tumors reached 50 mm³, usually 3 to 4 weeks after injection, mice were randomly selected for treatment with TCTP ASO alone, scrambled ASO alone, TCTP ASO plus docetaxel or scrambled ASO plus docetaxel. Mice bearing LNCaP tumors between 200 and 300 mm³ in volume were castrated via scrotal approach and randomly assigned to a treatment arm. Mice were treated beginning 1 week after castration with TCTP ASO or control ASO alone and serum PSA measurements were done weekly. For both experiments, each experimental group consisted in 10 mice and the tumor volume measurements were performed once weekly and calculated by the formula length×width×depth×0.5236 (Gleave et al., 1999, Clin Cancer Res 5:2891-8). After randomization, 10 mg/kg TCTP or scrambled ASO was injected intraperitoneally (i.p) once daily for 60 days for ASO monotherapy groups and 90 days for the ASO plus docetaxel groups. A total of 35 mg/kg docetaxel was administrated i.p. three times per week from days 7 to 14. Tumor volume measurements were performed once weekly and calculated by the formula length×width×depth×0.5236 (20). Data points were expressed as average tumor volume levels +/−standard error (SE). All animal procedures were performed in accordance with protocols approved by French laws and the European directives and with appropriate institutional certification.

Chemotherapeutic and Chemical Agents.

Docetaxel was obtained from Sanofi-aventis (Paris, France) and stock solution of docetaxel were prepared with DMSO to the required concentrations before each experiment. Cycloheximide and MG132 were purchased from Calbiochem (Merck Chemicals Ltd, Nottingham, UK).

Statistical Analysis.

All the results were expressed as mean+/−standard error (SE). Statistical analysis was performed using one-way analysis of variance followed by Fisher's protected least significant difference test (Statview 512, Brain Power Inc., Calabases, Calif., USA). *$P \leq 0.05$ was considered significant, with $P \leq 0.01$ and *$P \leq 0.001$.

Example 2

TCTP is a New Partner of Hsp27 that is Overexpressed in Castration-Resistant Prostate Cancer (CRPC)

To find a mechanistic explanation for the protective role of Hsp27 and identify new Hsp27 partners specific to CRPC, we used the CytoTrap approach to look for Hsp27 partner proteins. After, PubMed analysis of the identified partner proteins, we focused specifically on 4 partners: male-specific lethal-1 homolog (MSL-1), translationally-controlled tumour protein (TCTP), heterogeneous nuclear ribonucleoprotein A2/B1 (hnRNPA2B1) and S100 calcium binding protein A4 (S100A4). The expression level of these four partners was then performed on normal (PNT2C2), castration-sensitive (CS) LNCaP cell line and castration-resistant (CR) PC-3 and C4-2 cell lines and on human tissues. Proteins from normal (PNT2C2), CS LNCaP and CR PC-3 and C4-2 cells were extracted. TCTP and glyceraldehyde-3-phosphate dehydrogenase (GAPDH) protein levels were analyzed by western blotting. The results show that while TCTP was only slightly expressed in normal PNT2C2 cells, its expression strongly increased in CS LNCaP cells and even more in CR PC-3 and C4-2 cells. We found that neither hnRNPA2B1 nor S100A4 was overexpressed in the CR cell line PC-3.

It was also found that Msl-1 is slightly expressed in normal PNT2C2 cells, increases in LNCaP cells and becomes higher in CR PC-3 cells. However, in human samples Msl-1 was evenly expressed in normal and PC samples.

To investigate variations of TCTP levels after castration in PC xenograft, $10.10^6$ CS LNCaP cells were inoculated in athymic nude mice and when tumors were between 200 and 300 mm³ in volume, mice were castrated via scrotal approach. Tumors were harvested 0 and 40 days after castration. In parallel, $10.10^6$ CR C4-2 cells were inoculated in athymic nude mice and tumors were harvested 60 days after the inoculation. Proteins from LNCaP and C4-2 tumors were extracted. TCTP, Hsp27 and vinculin protein levels were analyzed by western blot analysis. The intensity of bands for TCTP and Hsp27 were normalized with vinculin and scoring with Image J software.

TCTP protein levels significantly increase in CR C4-2 xenograft (70%,  $P \leq 0.01$) compared to CS LNCaP xenograft (FIG. 1A). Furthermore, FIG. 1B show a 100% (*, $P \leq 0.001$) increase of TCTP expression in CR LNCaP xenograft harvested 40 days after castration compared to the CS tumors.

We then looked at TCTP expression in human samples using tissue microarray (TMA) of 131 non-treated specimens (see materials and methods). We found that TCTP was overexpressed in 10% of prostate adenocarcinoma (ADK). No expression was found in Benign Prostate Hyperplasia (BPH). It was found that than even in the normal glands disseminated inside of the tumors, no expression of TCTP was observed. In order to see the expression of TCTP during CR progression, we looked at TCTP expression in TMA of 232 castration-treated (CT) specimens (see materials and methods). TCTP expression was found to be down-regulated after androgen withdrawal to become uniformly highly expressed in CR metastasis. Specimens were graded from 0 to +3 intensity, representing the range from no staining to heavy staining by visual scoring and automated quantitative image analysis by proplus image software. Data from 232 samples were used to calculate (average) mean+/−SE. All comparisons of stain intensities were made at 200× magnification. The mean intensity of positive cells in the untreated, <3 months, 3 to 6 months, >6 months of CT, and CR was 1.8, 1.02, 0.8, 1.25, and 2.5, respectively (FIG. 1C).

Example 3

Hsp27 Protects TCTP from the Ubiquitin-Proteasome Degradation

Using confocal microscopy, we found that TCTP co-localizes with Hsp27 in the cytoplasm of LNCaP-Mock and -Hsp27 cells and that the intensity of TCTP staining and co-localization with Hsp27 was higher in LNCaP-Hsp27 as compared to Mock-transfected cells. Using co-immunoprecipitation (co-IP), we confirmed the interaction between Hsp27 and TCTP protein using LNCaP-Mock and -Hsp27 cell lysates and rabbit anti-TCTP or rabbit anti-Immunoglobulin (IgG) antibodies.

Figure 2:
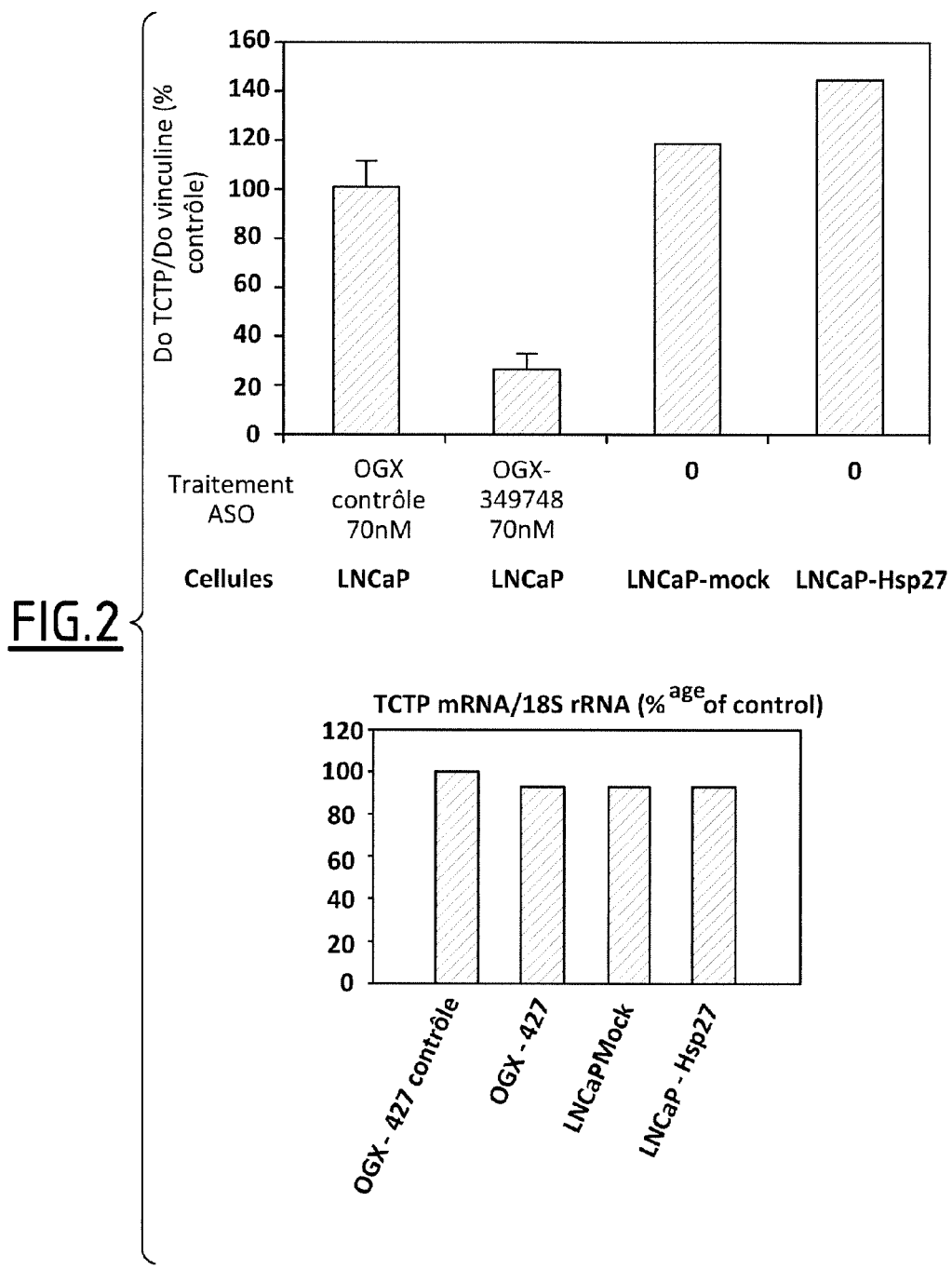
FIG. 2 illustrates TCTP expression level upon up- or down-regulation of Hsp27.

In order to understand the functional role of the interaction between Hsp27 and TCTP, we up- and down-regulated Hsp27 and checked TCTP level by western blot. We found that when Hsp27 is over-expressed the protein level of TCTP is 30% higher whereas LNCaP cells treated by OGX-427 show a TCTP protein level 70% lower than the LNCaP treated with the OGX-427-control (FIG. 2, upper panel) without any change on its mRNA expression level (FIG. 2, lower panel).

The results indicate that TCTP level correlates with that of Hsp27 and recent findings suggest that Hsp27 could affect the levels of its partner proteins by protecting them from their degradation by the ubiquitin-proteasome pathway (Andrieu et al., 2010, Oncogene. 29:1883-96).

To elucidate how Hsp27 regulates TCTP protein levels, we tested Hsp27 effect on rates of TCTP ubiquitination. Thus, ubiquitinated levels of TCTP were determined using co-immunoprecipitation in LNCaP-Mock and LNCaP-Hsp27 cells. It was found that overexpression of Hsp27 decreased ubiquitinated TCTP levels, as shown by the ladder of high-molecular-weight species, which is a characteristic of polyubiquitinated protein, suggesting that Hsp27 protects TCTP from its degradation by the ubiquitin-proteasome pathway.

To determine whether the ubiquitination of TCTP results in its proteasomal degradation, TCTP half-life was determined after OGX-427 treatment, in the presence or absence of the proteasome inhibitor MG132 and protein synthesis inhibitor cycloheximide after 2 days. Lysates from PC-3 cells, with or without MG132 (10 µmol/L) or cycloheximide (10 µg/ml), were analyzed by western blot, showing that MG132 treatment prolonged the half-life of TCTP and reversed the effect of OGX-427. This result demonstrates that down regulation of Hsp27 induces a decrease in TCTP protein level via its proteasomal degradation.

Figure 14:
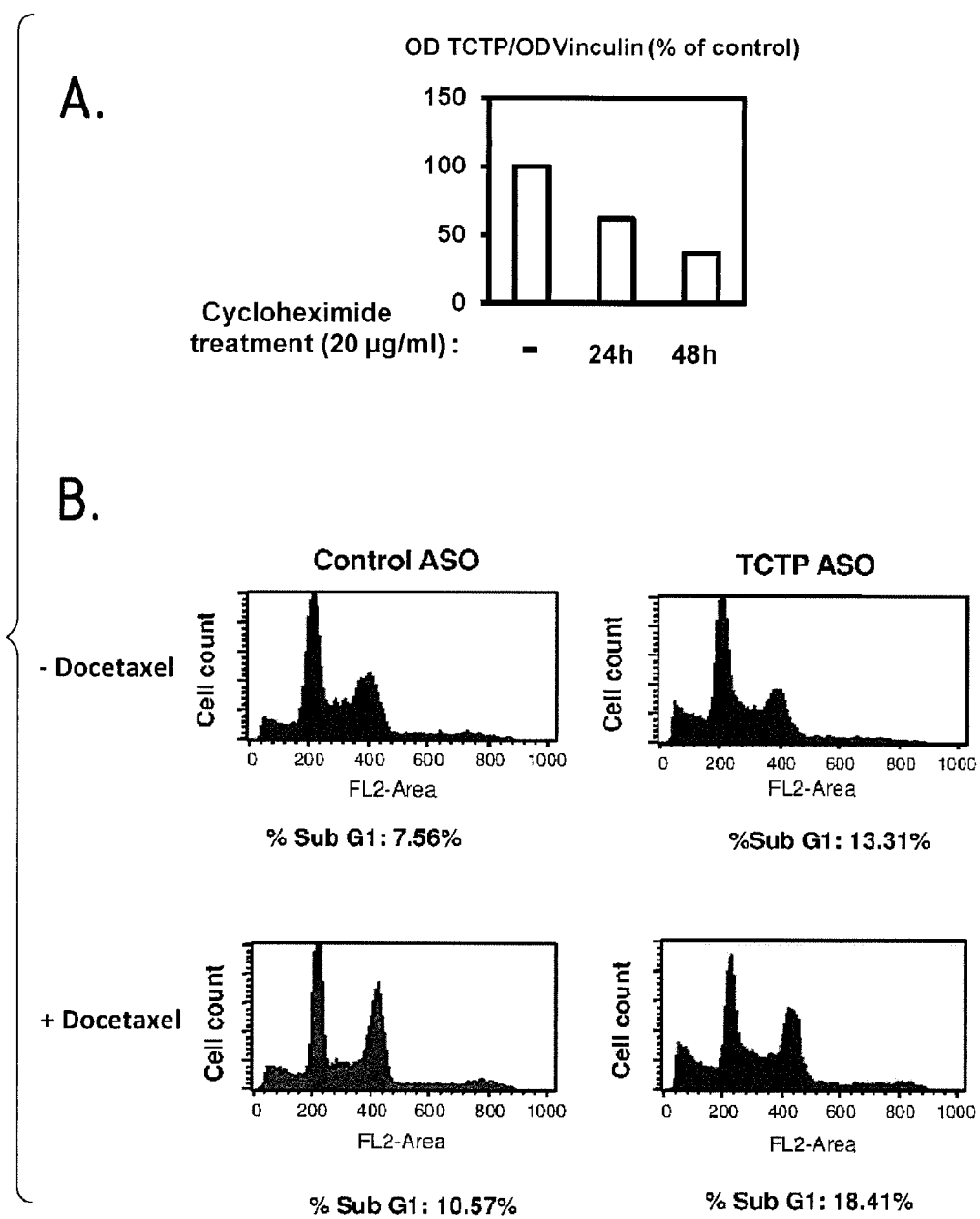
FIG. 14 illustrates TCTP half-life after cycloheximide treatment (A) and the percentage of PC-3 cells going to apoptosis after TCTP ASO treatment.

These results are supported by the fact that after cycloheximide treatment alone (20 µg/ml), TCTP protein levels decrease time dependently by 40% and 60% at 24 h and 48 h respectively. Indeed, these results are observed on FIG. 14A showing TCTP signal (normalized with vinculin and scoring with Image J software) of a western blotting analysis of cell lysates of PC-3 cells after 24 h and 48 h treatment with 20 µg/ml of cycloheximide.

Example 4

TCTP siRNA Decreases the Hsp27 Cytoprotective Effects

To study the functional role of TCTP in CRPC, siRNA-induced inhibition of TCTP expression was used to determine whether the reduction of TCTP expression affects LNCaP-Mock and -Hsp27 cell growth after combined androgen withdrawal and docetaxel-chemotherapy treatment in vitro. The cytoprotection induced by Hsp27 overexpression in LNCaP cells seems to involve TCTP activity, as TCTP knockdown using siRNA 5 nM reversed the cytoprotection to androgen withdrawal and docetaxel treatment normally conferred by Hsp27 overexpression.

Figure 3:
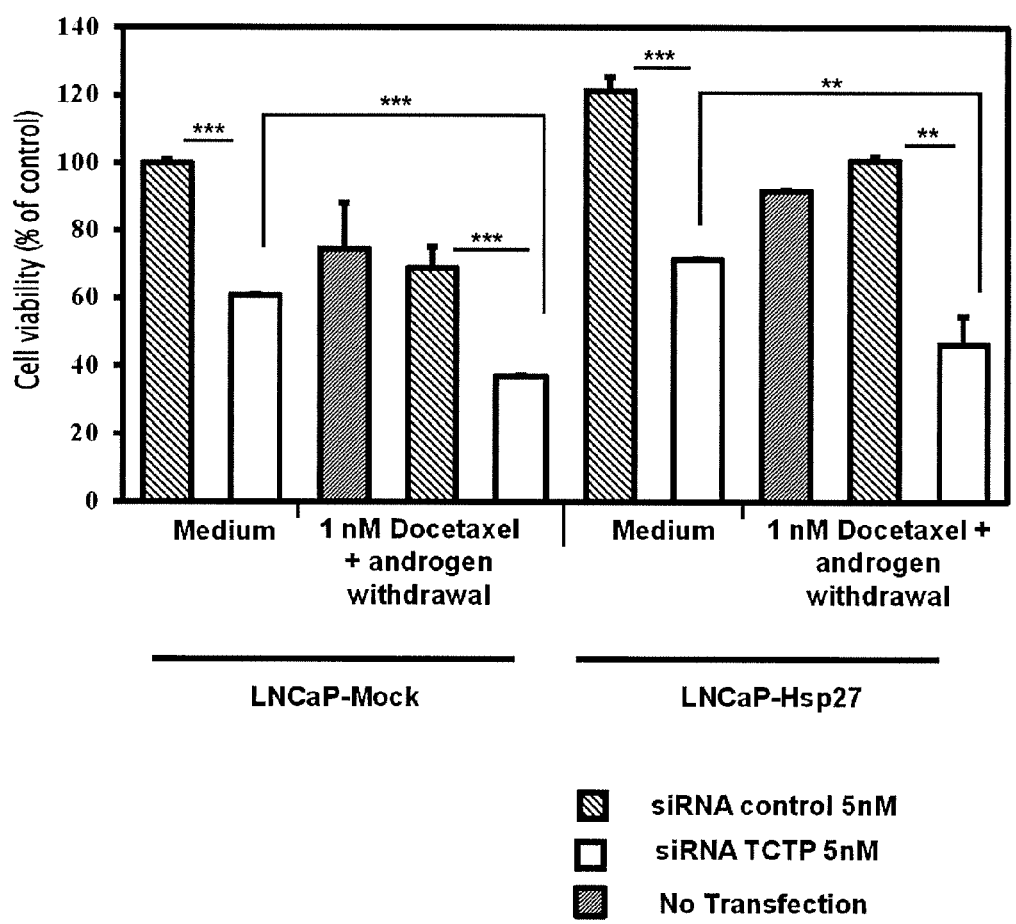
FIG. 3 illustrates the effect of TCTP expression on LNCaP-Mock and -Hsp27 cell viability.

In order to study consequences of TCTP inhibition on cell survival after combined androgen withdrawal and docetaxel-chemotherapy treatment, cell viability of LNCaP-Mock and -Hsp27 was determined using crystal violet dye after 24 h treatment with 1 nM of docetaxel in serum-free media (mimics androgen withdrawal in vitro). This analysis demonstrates that TCTP inhibition decreases LNCaP-Mock and -Hsp27 cell survival after combined androgen withdrawal and docetaxel-chemotherapy treatment. Indeed, FIG. 3 shows a 50% (*, P≤0.001) reduction in LNCaP-Hsp27 cell growth rate versus 40% (*, P≤0.001) in LNCaP-Mock after TCTP down regulation (siRNA 5 nM) compared with control. After TCTP siRNA plus docetaxel in serum-free medium treatment (mimics androgen withdrawal in vitro), we found an 80% (, P≤0.01) reduction in LNCaP-Hsp27 cell growth rate versus a 50% (, P≤0.01) reduction in LNCaP-Mock compared to control.

Example 5

ASO Sequences Screening

In order to find a sequence ASO having an inhibiting effect on TCTP expression, 30 ASO sequences have been designed 26 of which are shown in table 1. Said 30 sequences cover the TCTP mRNA (accession number NM_003295). Using BLAST program, the specificity of said sequences has been studied. Among said 30 sequences, only 15 sequences have been identified as being specific for TCPT mRNA sequence (see table 1). The effect of said ASO sequences on TCTP expression was tested by western blot analysis (WB) and/or by quantitative reverse transcription polymerase chain reaction (qRT-PCR) on PC-3 cells overexpressing TCTP. WB and qRT-PCR were performed as exposed in example 1.

TABLE 1

| ASO No | Sequences | Sequence number SEQ ID NO:: | Specificity |
|---|---|---|---|
| 4 | TAATCATGATGGCGACTGAA | 17 | yes |
| 5 | GCTGATGAGGTCCCGGTAGA | 18 | no |
| 6 | TCGGAGAACATCTCATCGTG | 19 | no |
| 7 | CAGGCACAACCCGTCCGCGA | 20 | no |
| 8 | ACCATCTTCCCCTCCACCTC | 21 | no |
| 9 | TGTTACCTTCTGTCCTACTG | 22 | yes |
| 10 | ACCAATGAGCGAGTCATCAA | 2 | yes |
| 11 | CCTTCAGCGGAGGCATTTCC | 23 | no |
| 12 | CAGTACCTTCGCCCTCGGGG | 24 | no |
| 13 | ACCAGTGATTACTGTGCTTT | 25 | yes |
| 14 | TGGTTCATGACAATATCGAC | 15 | yes |
| 15 | AACTTGTTTCCTGCAGGTGA | 14 | yes |
| 16 | CTTGTAGGCTTCTTTTGTGA | 26 | yes |
| 17 | ATGTAATCTTTGATGTACTT | 27 | yes |
| 18 | GTTTCCCTTTGATTGATTTC | 28 | yes |
| 19 | TTCTGGTCTCTGTTCTTCAA | 29 | yes |
| 20 | ATAAAGAACTGGTAGTTTTT | 30 | no |
| 21 | CTGGATTCATGTTTTCACCA | 31 | no |
| 22 | CAATAGAGCAACCATGCCAT | 32 | no |
| 23 | ACACCATCCTCACGGTAGTC | 33 | no |
| 24 | AGAAAATCATATATGGGGTC | 34 | yes |
| 25 | CATTTCTAAACCATCCTTAA | 35 | yes |
| 26 | TTAACATTTCTCCATTTCTA | 36 | yes |
| 27 | TCTCCCGGATCTTGTAGATG | 37 | no |
| 28 | GTCATAAAAGGTTTTACTCT | 38 | yes |

TABLE 1-continued

| ASO No | Sequences | Sequence number SEQ ID NO:: | Specificity |
|---|---|---|---|
| 29 | TGATTTGTTCTGCAGCCCCT | 39 | no |
| 30 | GAAATTAGCAAGGATGTGCT | 40 | yes |

ASO sequences ASO4 of sequence SEQ ID NO: 17, ASO10 of sequence SEQ ID NO: 2, ASO13 of sequence SEQ ID NO: 25, ASO14 of sequence SEQ ID NO: 15, ASO15 of sequence SEQ ID NO: 14, ASO16 of sequence SEQ ID NO: 26, ASO17 of sequence SEQ ID NO: 27, ASO18 of sequence SEQ ID NO: 28, ASO19 of sequence SEQ ID NO: 29, ASO24 of sequence SEQ ID NO: 34, ASO26 of sequence SEQ ID NO: 36, ASO28 of sequence SEQ ID NO: 38 and ASO30 of sequence SEQ ID NO: 40 show a strong ability to inhibit TCTP expression. And ASO 10 sequence having the sequence of SEQ ID NO: 2 (5'-ACCAATGAGCGAGTCATCAA-3'), ASO 15 sequence having the sequence of SEQ ID NO: 14 (5'-AACTTGTTTC-CTGCAGGTGA-3'), and ASO 14 sequence having the sequence of SEQ ID NO: 15 (5'-TGGTTCAT-GACAATATCGAC-3') manifest the best ability to inhibit specifically TCTP expression (see table 1).

Example 6

TCTP ASO and siRNA Treatment Inhibits CR PC-3 Cell Growth and Enhances Chemotherapy In Vitro Studies have demonstrated that TCTP is highly expressed in several cancers like colon (Chung et al., 2000, Cancer Lett. 156:185-190), breast (Deng et al., Genomics Proteomics Bioinformatics. 2006, 4:165-72) or prostate tumors (Tuynder et al., 2002, Proc Natl Acad Sci USA 99:14976-14981; Arcuri et al., 2004, Prostate 60:130-140). In biological models of tumor reversion established from human leukemia and breast cancer cell lines, TCTP was found to be the most strikingly down-regulated in tumor reversion (Tuynder et al., 2002, Proc Natl Acad Sci USA 99:14976-14981). Furthermore, Tuynder et al., demonstrated that the inhibition of TCTP expression could induce changes in the malignant phenotype, when the viral-sarcoma (v-src) transformed NIH3T3 cells were transfected with antisense TCTP (Tuynder et al., 2004, Proc. Natl. Acad. Sci. U.S.A. 101: 15364-15369).

Figure 4:
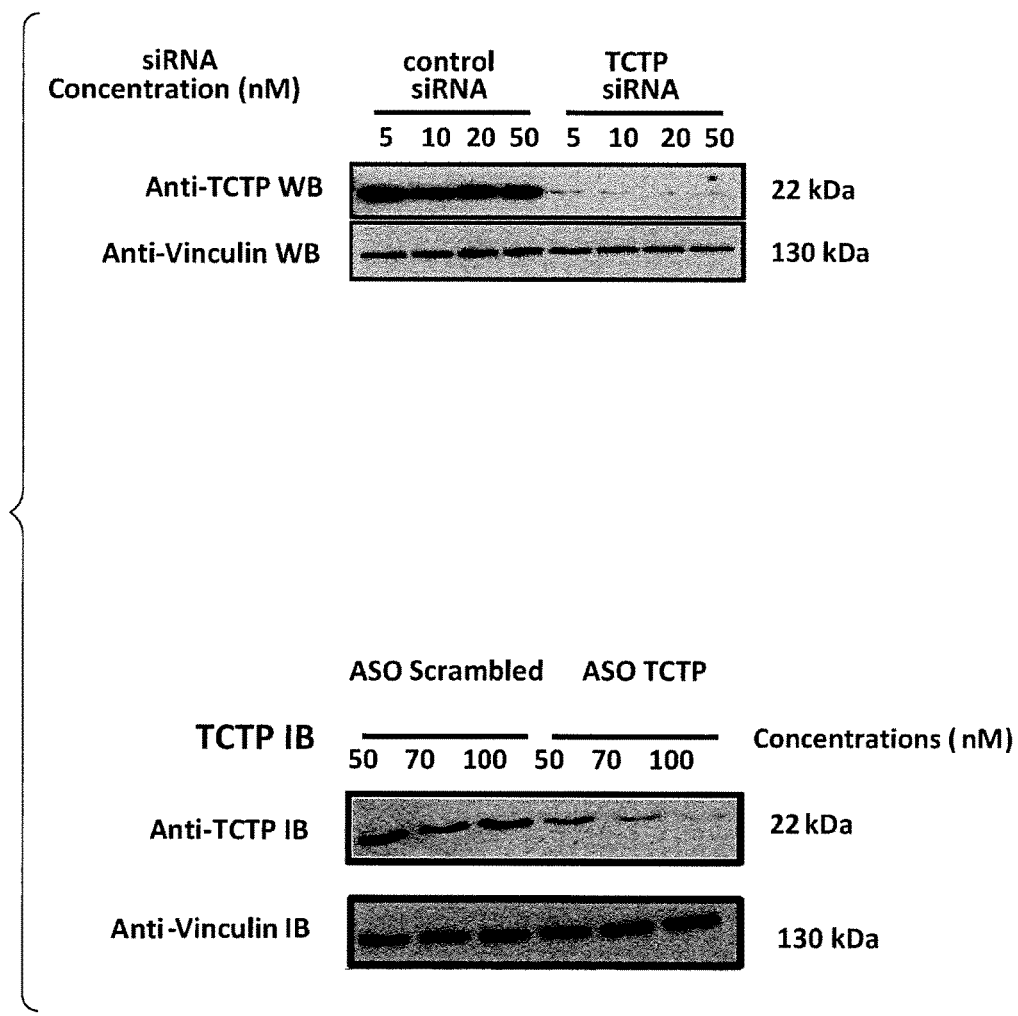
FIG. 4 shows TCTP protein expression in PC3 cells transfected with TCTP siRNA or ASO.
Figure 5:
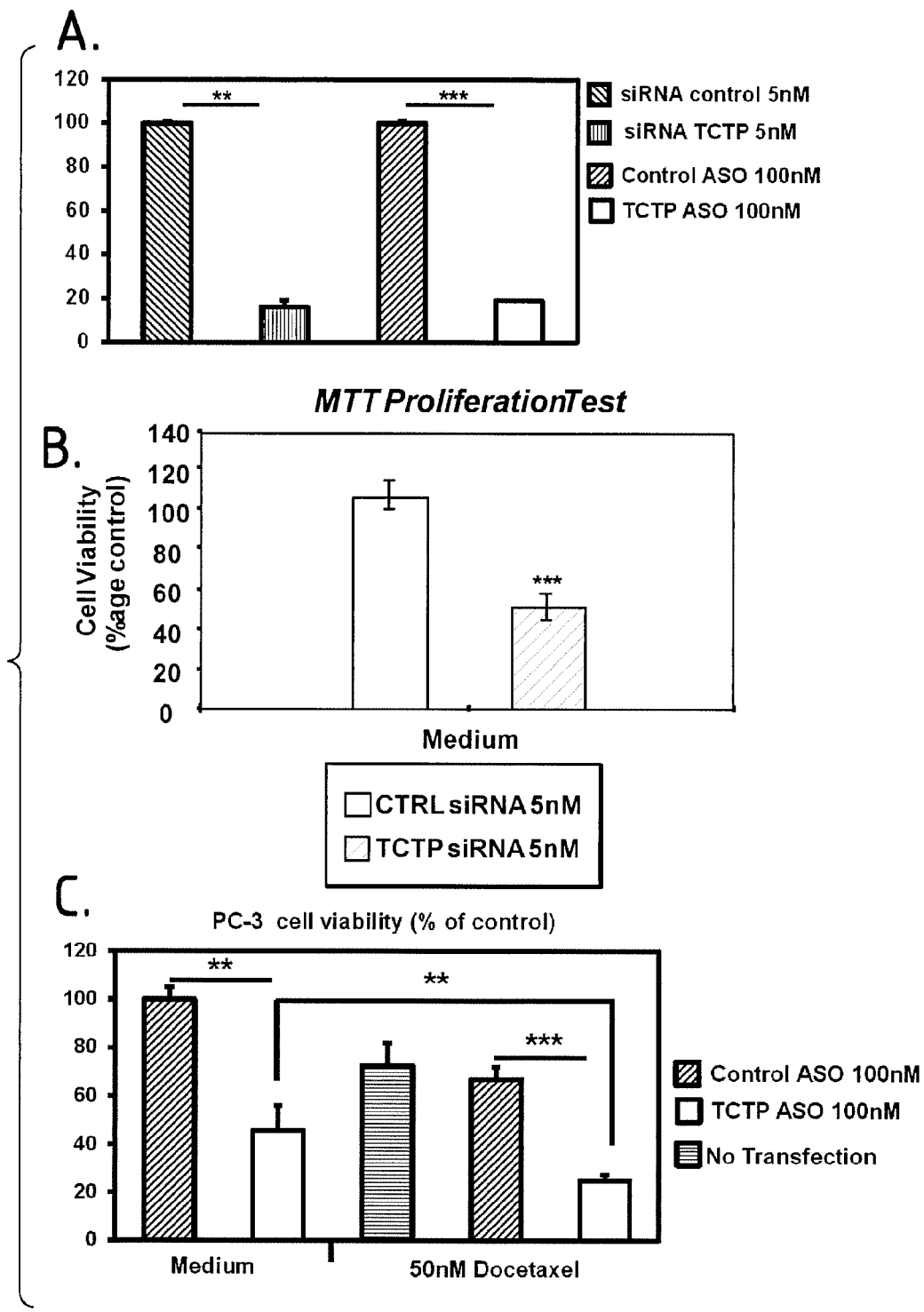
FIG. 5 illustrates the effect of TCTP inhibition on PC-3 cell viability.

To determine whether the inhibition of TCTP expression affects CR progression in vitro, ASO- or siRNA-induced inhibition of TCTP expression was determined by Western blot analysis. Proteins were extracted from PC-3 cells treated with 5 to 50 nM of siRNA TCTP or 50 to 100 nM of ASO TCTP or ASO Scrambled showing that significant inhibition of TCTP protein was observed after siRNA or ASO treatment at 5 and 100 nM respectively. Similar results were observed for TCTP mRNA levels (FIG. 4). TCTP mRNA was obtained from PC-3 cells treated for 1 day with 5 nM of TCTP- or control-siRNA, and for 2 days with 100 nM of ASO TCTP or an ASO control. Total RNA was extracted and TCTP levels were analyzed by qRT-PCR. After the normalization of TCTP mRNA with 18S rRNA levels, results were analysed with the 2(-Delta Delta C(T)) Method (FIG. 5A). Each sample was analyzed in triplicate.  differs from PC-3 transfected with control-siRNA (P≤0.01) and * with ASO control (P≤0.001) using Statview software.

To assess the effect of TCTP down-regulation on CR cell growth, PC-3 cells were treated for 1 day with 5 nM TCTP siRNA or for 2 days with 100 nM TCTP ASO. At the end of the treatment, PC-3 cells were incubated with 50 nM of docetaxel. Growth rates of PC-3 cells were examined using the 3-(4,5-dimethylthiazol-2-yl)-2,5-diphenyltetrazolium bromide assay. FIG. 5B, shows a 55% (*, P≤0.001) reduction in PC-3 cell growth 4 days after treatment with TCTP 5 nM siRNA alone compared to scrambled control. Similar growth inhibition was observed with 100 nM TCTP ASO (FIG. 5C). The effect of the inhibition of TCTP on cell survival was analyzed in PC-3 after combined ASO and docetaxel-chemotherapy treatment. After 24 h of treatment with 50 nM of docetaxel, cell viability was determined using a MTT assay. The experiment was repeated in triplicate. * differs from PC-3 transfected with control-siRNA (P50.001) using Statview software. Furthermore, FIG. 5C, also shows that TCTP down-regulation using ASO treatment can enhance docetaxel sensitivity by up to 25%. The same effect has been observed with TCTP siRNA (SEQ ID NO: 3) and 5'-AACTTGTTTCCTGCAGGTGA-3' (SEQ ID NO: 14) and 5'-TGGTTCATGACAATATCGAC-3' (SEQ ID NO: 15) ASOs.

Figure 15:
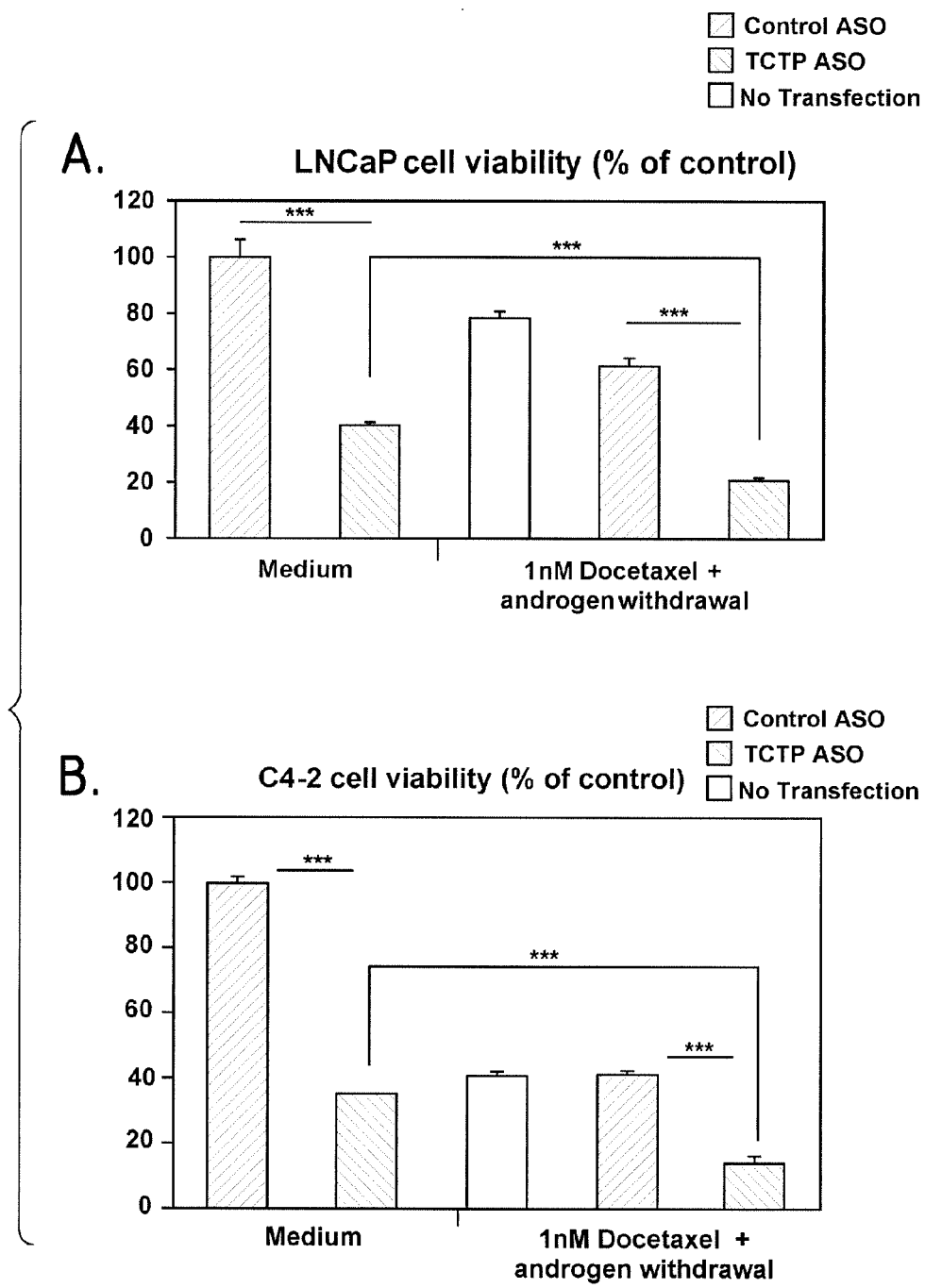
FIG. 15 illustrates the effect of TCTP inhibition on LNCaP and C4-2 cell viability
Figure 16:
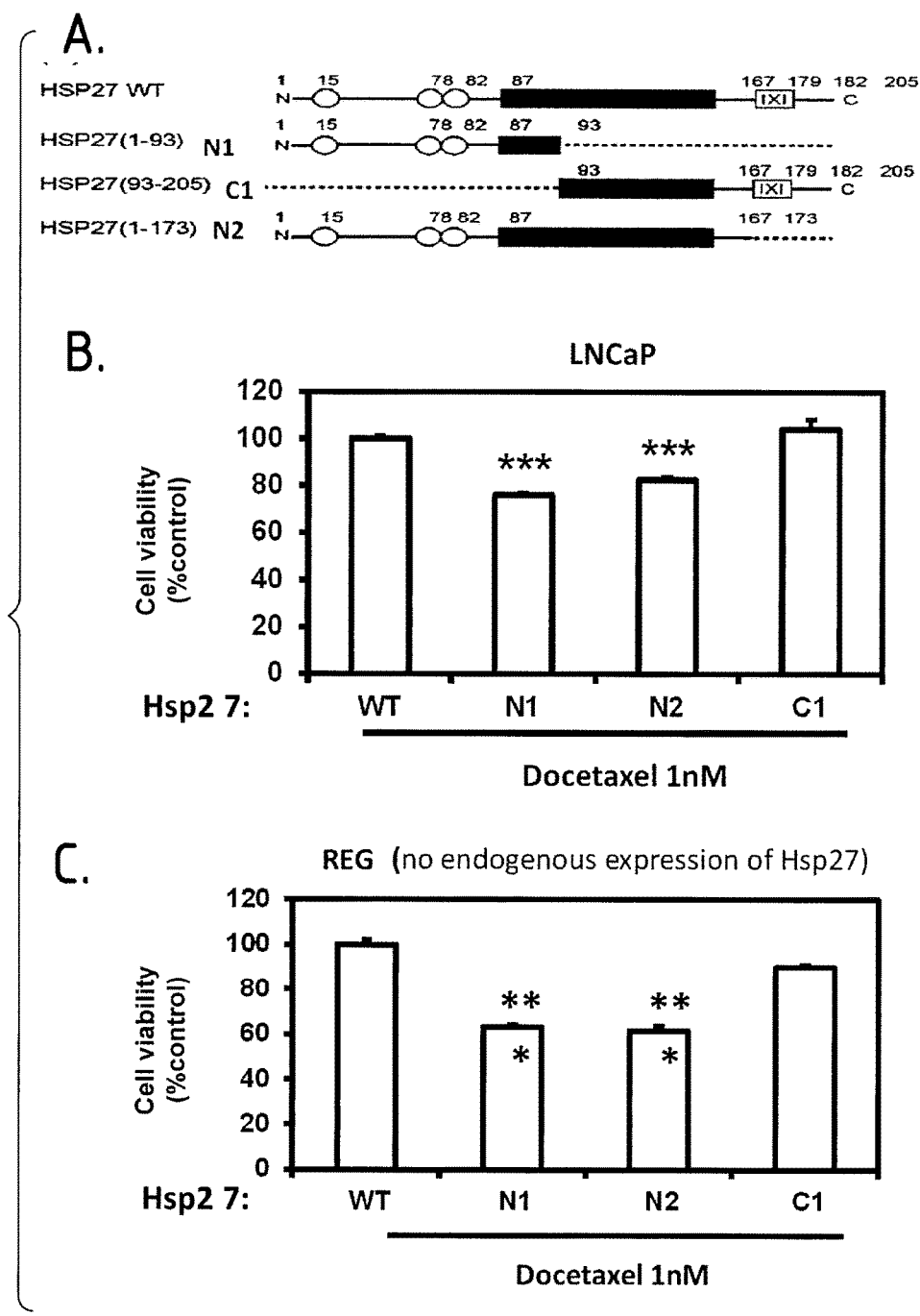
FIG. 16 illustrates Hsp27 N-terminal or C-terminal mutants' ability to interact with TCTP.
Figure 17:
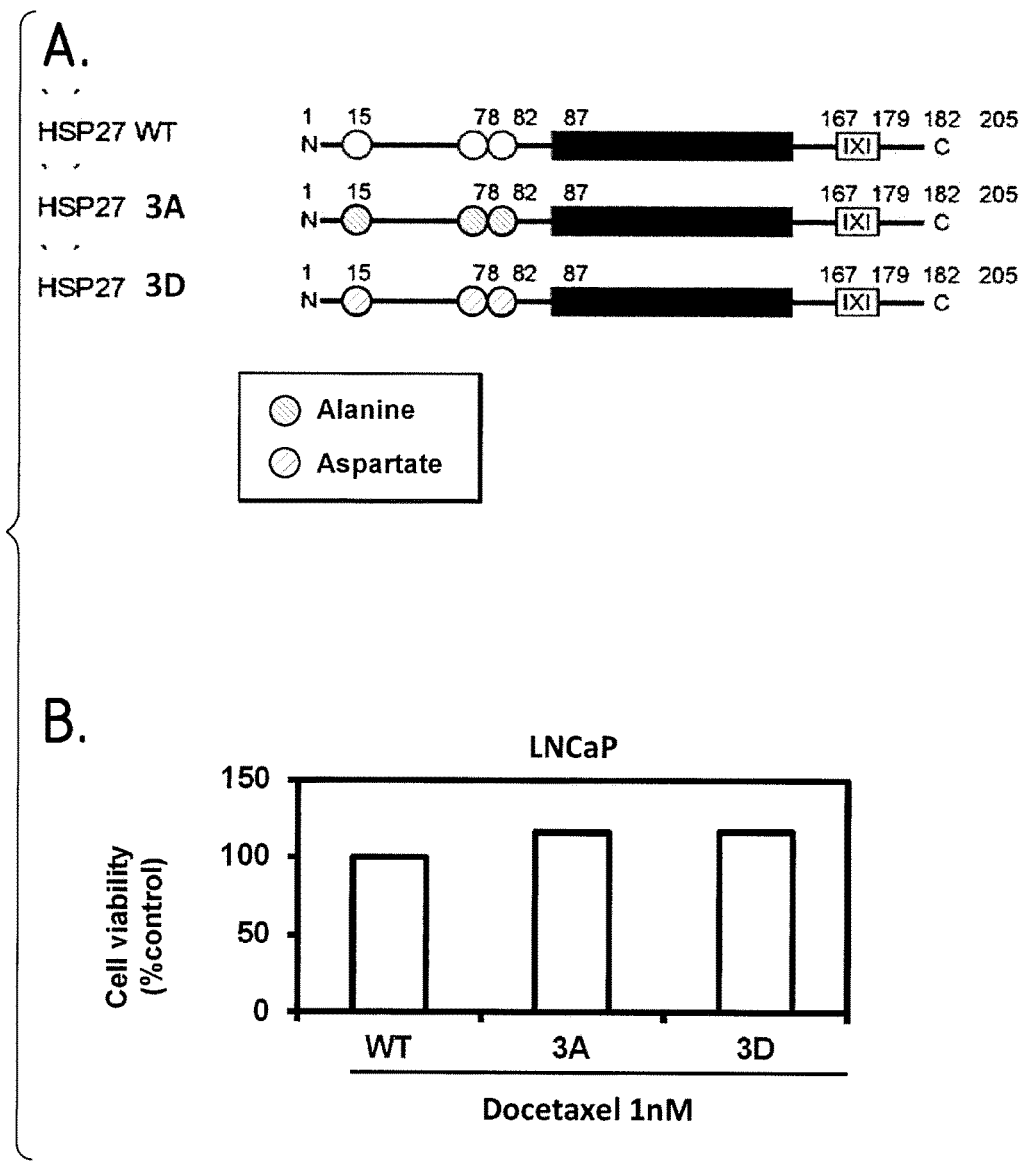
FIG. 17 illustrates Hsp27 phosphorylation mutants' ability to interact with TCTP

Finally, in order to assess if TCTP ASO has the same effect on prostatic cancer cell lines expressing the androgen receptor (AR), crystal violet dye was used to examin LNCaP and C4-2 cell growth. LNCaP and C4-2 were treated with 100 nM TCTP or control ASO (FIGS. 15 A and B) for 2 days. Then, LNCaP and C4-2 cells were incubated with 1 nM of docetaxel in serum-free media. This result clearly show that TCTP down-regulation considerably decrease LNCaP and C4-2 cell growth and enhance treatments (docetaxel and androgen withdrawal) sensitivity.

Example 7

TCTP ASO and siRNA Treatment Induces Apoptosis in PC-3 Cells in Vitro

Figure 6:
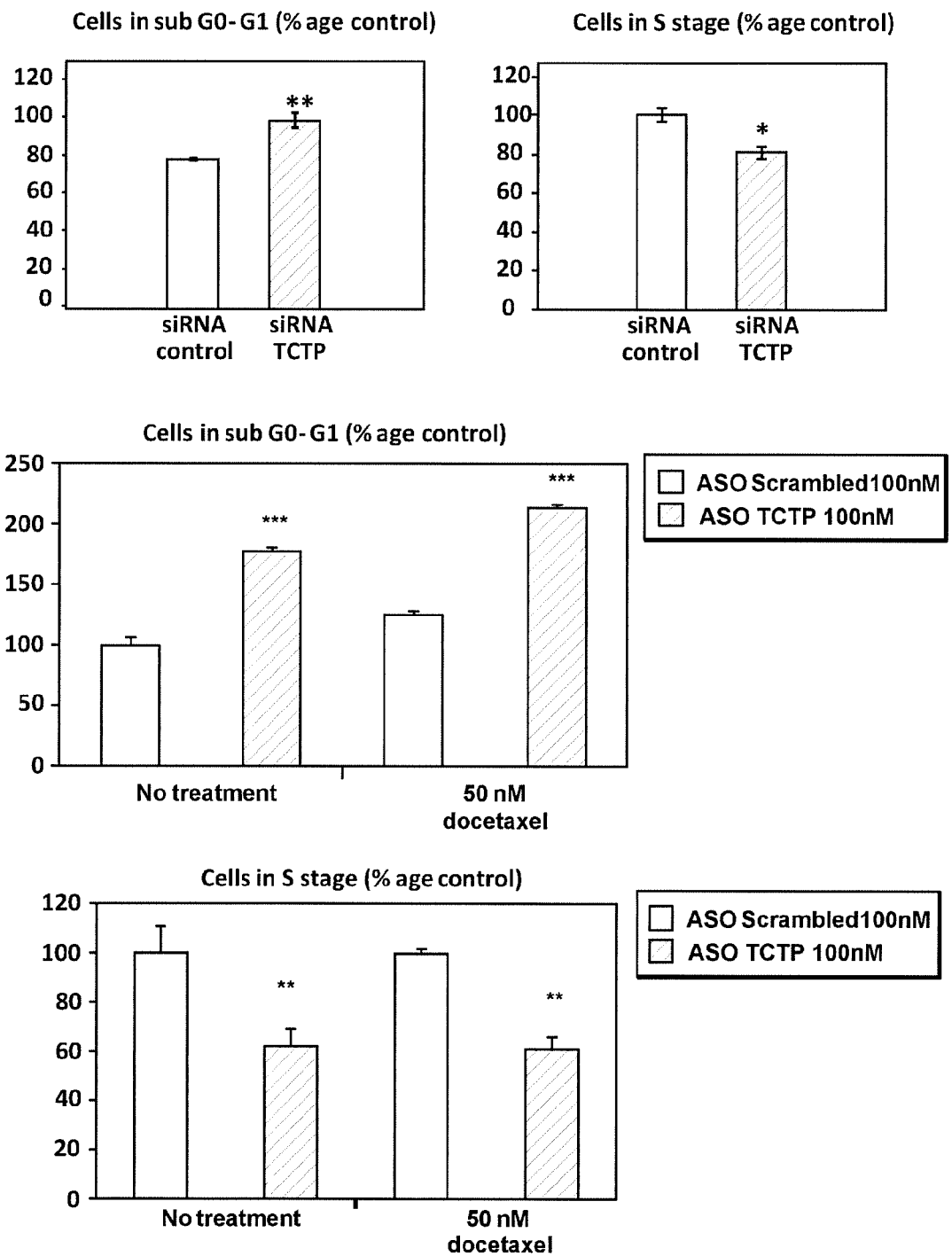
FIGS. 6 and 7 illustrate the rate of apoptotic PC-3, LNCaP and C4-2 cells after TCTP inhibition.
Figure 7:
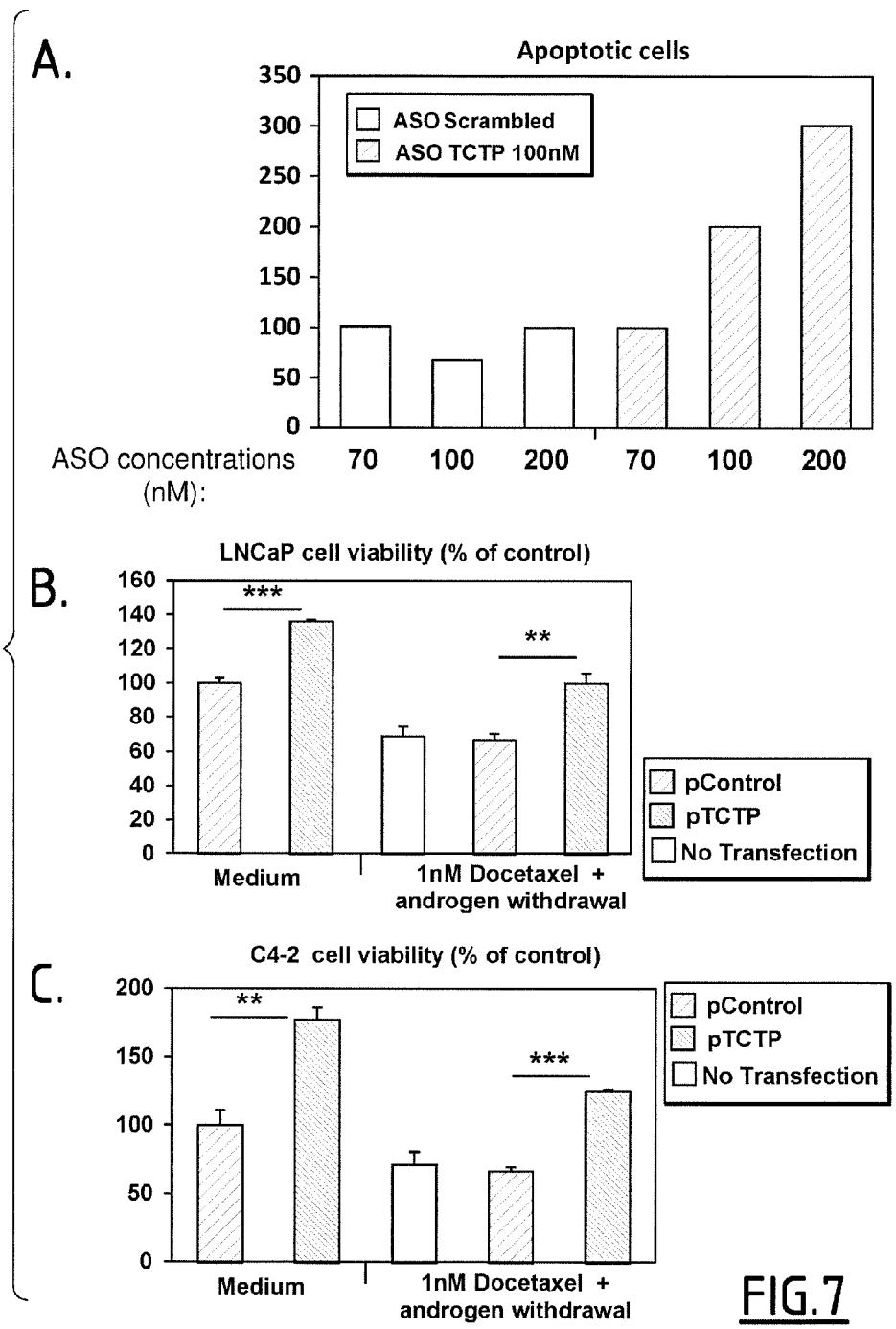

Induction of apoptosis and cell cycle blocking by TCTP ASO or siRNA was demonstrated by flow cytometry. Flow cytometry was used to quantify the percentage of cells in each cell cycle phase three days after the siRNA treatment. After the treatment of PC-3 cells with 5 nM TCTP siRNA for 1 day, the fraction of cells undergoing apoptosis (sub-G1/G0 fraction) was 25% higher after treatment with 5 nM TCTP siRNA compared with scrambled control siRNA (, P≤0.01; FIG. 6, upper panel). Using TCTP ASO treatment alone, we found an increase of 75% in sub-G0G1 fraction (*, P≤0.001; FIG. 6, middle and bottom panel), enhanced by the 50 nM docetaxel treatment (90% in sub-G0-G1 fraction, ***, P≤0.001). We also found that the inhibition of TCTP decreased the number of cells in the S phase. The fraction of PC-3 in S phase was 20 to 40% lower after TCTP siRNA or ASO treatments respectively compared to the scrambled controls (FIG. 6). These results clearly demonstrate an increased apoptotic rate and a cell cycle arrest associated with TCTP silencing. We observed that the docetaxel treatment increased the fraction of cells undergoing apoptosis without changing the fraction of cells in S phase. The rate of apoptotic PC-3 cells after TCTP silencing with different ASO concentrations was explored with the Invitrogen countess (FIG. 6 and FIG. 7A). PC-3 cells were treated with 70, 100 or 200 nM of TCTP ASO or control.

Cells were harvested 3 days after treatment and 10 ml of trypan blue was added before analysis with Invitrogen Countess. The results showed that three days after the PC-3 transfection with 70, 100 and 200 nM of TCTP or scrambled control ASO, the rate of apoptotic cells was 100, 200 and 300% respectively. Same effects were observed with TCTP siRNA. Moreover, TCTP has been reported to interact with caspase-3, thereby inhibiting caspase-3 activation (Gnanasekar et al., 2009, Int J Oncol. 34:1241-6). In order to investigate the effect of TCTP silencing on caspase-3 cleavage and activity, PC-3 cells were treated daily with 100 nM TCTP or scrambled ASO for 2 days. Cells were harvested 2 days after and proteins were extracted for western blotting with a caspase-3 antibody that recognizes both full-length and cleaved caspase-3. The western blot reveals the presence of active cleaved caspase-3 fragments (17-20 kDa) only in PC-3 cells treated with TCTP ASO or TCTP siRNA but not in the control treated cells.

Example 8

TCTP Overexpression Confers Chemoresistance in LNCaP and C4-2 Cells

To better address the role of TCTP in chemosensitivity, C4-2 and LNCaP cells were transiently transfected with pDEST-TCTP or pDEST-control vectors. After 48 h treatment with 1 nM of docetaxel in serum-free media (which mimics androgen withdrawal in vitro), cell viability was determined using the crystal violet assay. The results obtained clearly indicate that LNCaP and C4-2 cells overexpressing TCTP had increased cell survival after combined androgen withdrawal and docetaxel-chemotherapy treatment. Indeed, TCTP clearly seems to have a role on cell chemosensitivity as its overexpression lead to a 40% (, P≤0.01) and 60% (*, P≤0.001) increase in LNCaP and C4-2 viability respectively (FIG. 7B and FIG. 7C) after 1 nM docetaxel in serum free medium treatment.

Example 9

Figure 8:
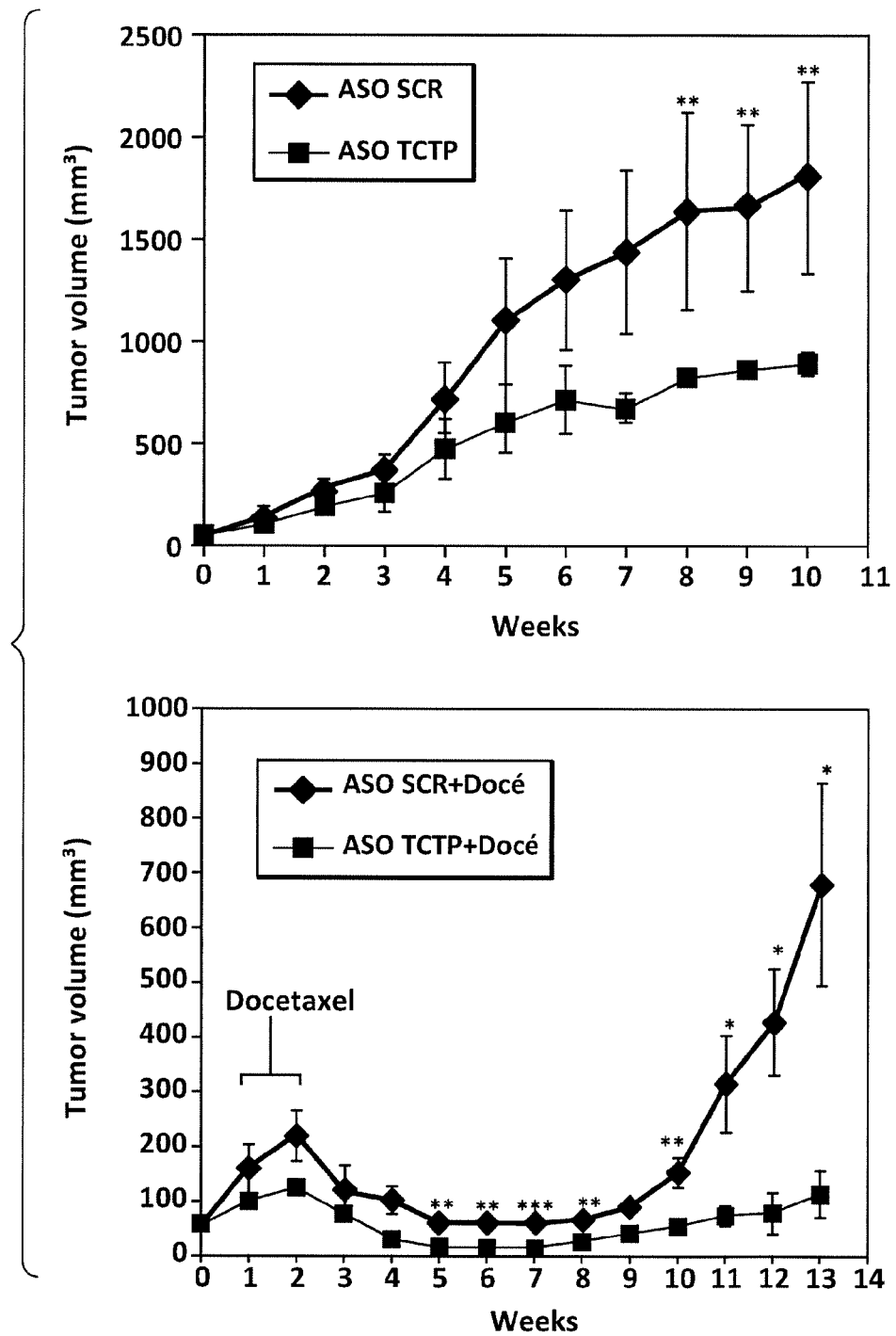
FIG. 8 illustrates the anticancer activity of TCTP ASO on PC3 xenografted tumor volume (upper panel) and its additive activity with docetaxel (bottom panel).

TCTP ASO Treatment Inhibits PC-3 Tumor Progression and Enhances Chemotherapy In Vivo We next evaluated the effects of TCTP ASO treatment on the growth of PC-3 tumors in vivo (FIG. 8). Male nude mice bearing PC-3 tumors (50 mm$^3$) were randomly selected for TCTP ASO versus scrambled ASO and 10 mg/kg ASO were administrated once daily by i.p. injection for 70 days. From days 7 to 14, 30 mg/kg of docetaxel was administrated i.p. 3 days in the week. Mean tumor volume was similar in all groups before therapy.

Figure 9:
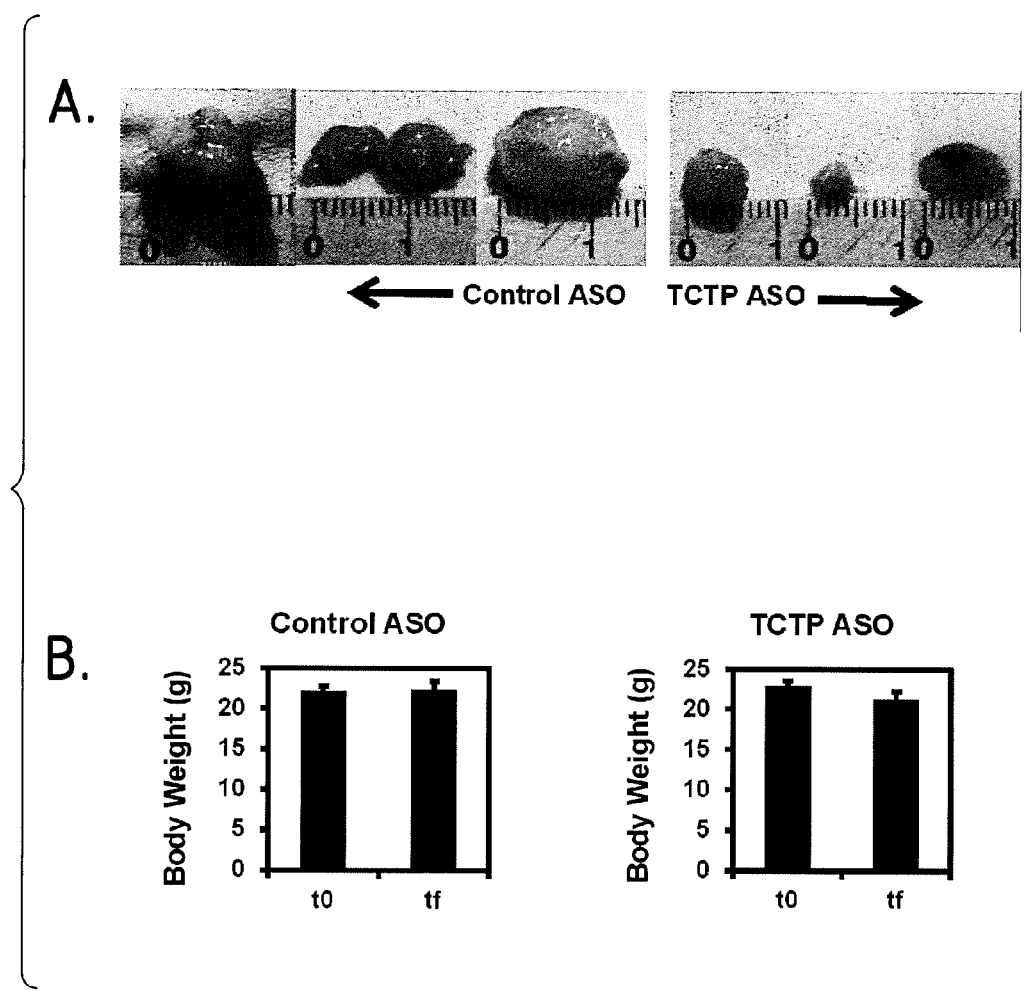
FIG. 9 illustrates the effect of TCTP ASO treatment on PC-3 tumor growth and docetaxel chemosensitivity in vivo.

FIG. 8, upper panel (Points, mean tumor volume in each experimental group containing 10 mice; bars, SE. *;  and * differ from scrambled control (p≤0.05; p≤0.01 and p≤0.001, respectively) by Statview software) shows that TCTP ASO monotherapy significantly reduced PC-3 tumor volume by 50% from days 56 to 70 (**, P≤0.01) Measurements of harvested tumors from animals that received ASO TCTP or control by i.p. during two weeks clearly show that harvested tumors from animals treated with TCTP ASO also tended to be 50% smaller in appearance after two weeks of treatment (FIG. 9A). Moreover, treatment with TCTP ASO, compared with scrambled control, significantly enhanced the apoptotic effects of docetaxel in vivo, reducing mean PC-3 tumor volume by <70% by %, 13 weeks after initiation of treatment (*, P≤0.05; FIG. 8, lower panel).

In order to see if apoptosis was observed in tumors treated with ASO TCTP, proteins were extracted from harvested PC-3 tumors treated with ASO TCTP or control alone. The presence of cleaved caspase-3 fragments observed by western blotting analysis only in tumors treated with TCTP ASO clearly demonstrates that the i.p. delivery of TCTP ASO increased apoptosis.

The absence of toxicity of the treatment on animals was studied by measuring their body weight before the first injection (t0) and the day of sacrifice (tf) (FIG. 9B). Under the experimental conditions described above, no adverse effects were observed. Indeed, FIG. 9B shows that TCTP ASO did not cause general toxicity to animals indicated by no change in animal behavior or body weight.

Example 10

TCTP ASO of SEQ ID NO: 2 Delay LNCaP Tumor Progression after Castration In Vivo

Figure 10:
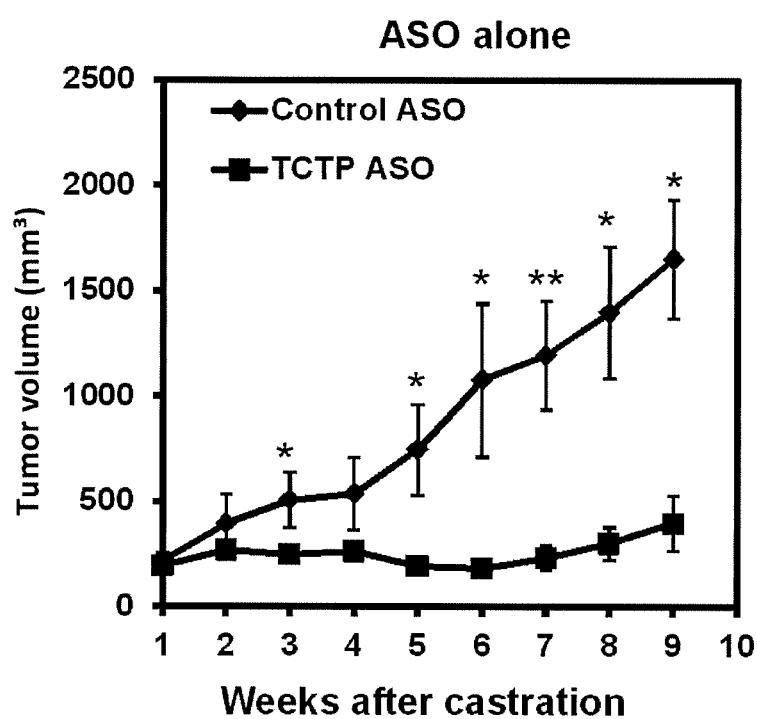
FIGS. 10 and 11 illustrate the effect of TCTP ASO treatment on LNCaP tumor growth in vivo after castration
Figure 11:
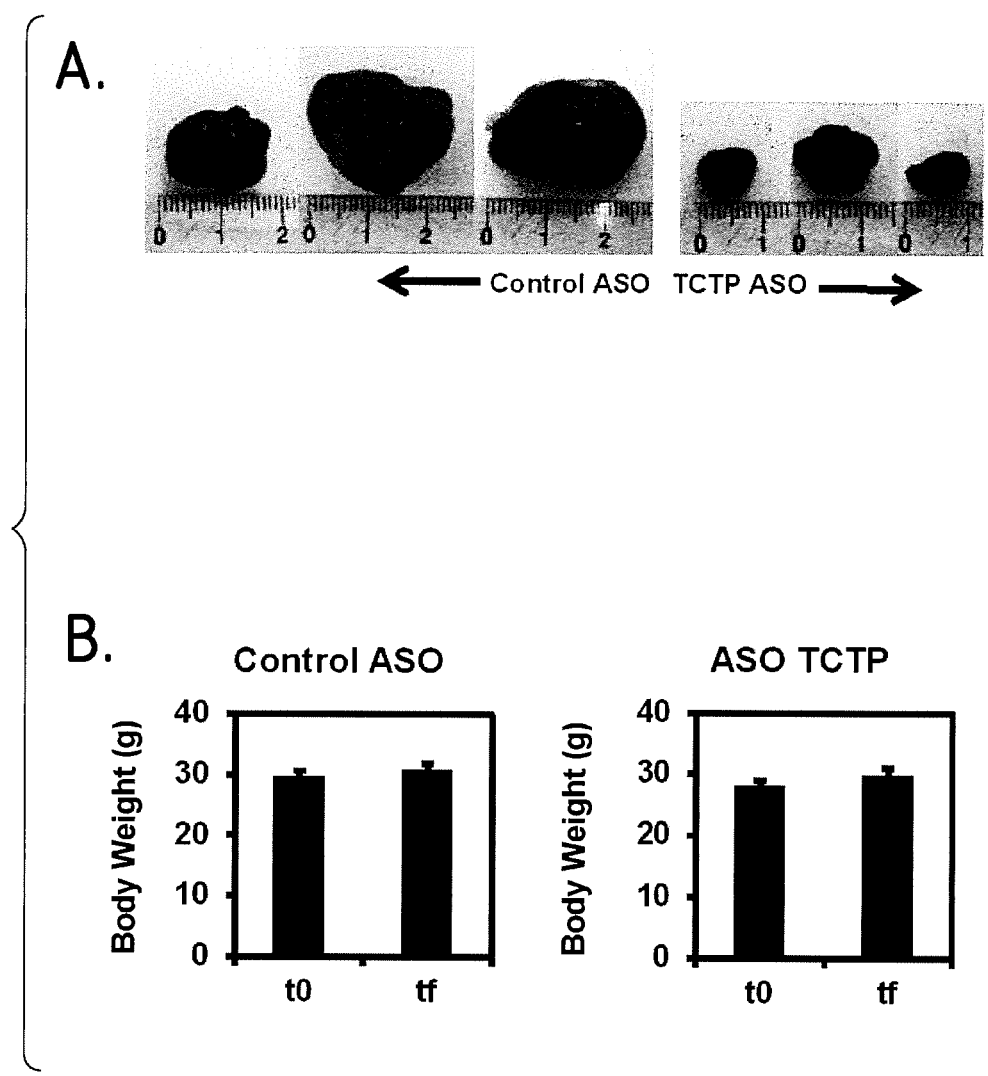

Twenty male mice bearing LNCaP tumors were castrated 6 to 8 weeks after tumor implantation and were randomly selected for treatment with TCTP ASO of SEQ ID NO: 2 versus control ASO. Castration was done when tumors reached a mean of 200 mm3. Mean tumor volume and PSA were similar in both groups at the beginning of the treatment. Beginning 1 week after castration, 10 mg/kg of ASO was administered once daily by i.p. injection for 9 weeks. As shown in FIG. 10, LNCaP tumor volume increased more slowly in mice treated with TCTP ASO, compared with those treated with control ASO. All mice (n=10) treated with castration plus TCTP ASO had a significant inhibition of AI tumor growth during the 9 weeks of analysis. At sacrifice, tumor volume was 4-fold higher in control (1650, 15±281, 76 mm$^3$) compared with the TCTP ASO-treated group (397, 79±132, 61 mm$^3$; *, P≤0.05). Photographs of harvested tumors from animals that received ASO TCTP or control during 9 weeks (FIG. 11A) shows that tumors harvested were ¾-fold smaller in appearance after 9 weeks of TCTP ASO monotherapy. No side effects were observed with TCTP ASO or control treatment as indicated by no change in animal behavior or body weight (body weight before the first injection (t0) and body weight the day of sacrifice (tf)) (FIG. 11B).

Example 11

Summary of the Results

Effect of Compounds on TCTP mRNA and Protein Expression in Prostate Cancer Cells Staining of TCTP was done in tissue microarrays (TMA) from 335 patients suffering from one of the following diseases:
Benign Prostatic Hyperplasia (BPH);
Prostate cancer with a Gleason score of ¾, wherein the patients has not been treated; or
Castration-resistant (CR) liver, bone and lymph node prostate cancer (PC) metastasis.

No expression of TCTP was found in BPH and normal glands of the prostate and only 10% of Gleason ¾ PC express TCTP before castration. However, TCTP was found to be highly and homogeneously overexpressed in CR metastatic PC. TCTP expression was also found slightly expressed in normal prostate cell line immortalized with simian virus SV40 (PNT2C2). Overexpression of TCTP was found in CRPC cells (PC3) compare to castration-sensitive (CS) cells LNCaP.

TCTP mRNA and protein expression tests were carried out in LNCaP and PC3 cells exposed to a TCTP ASO of SEQ ID NO: 2 or a TCTP siRNA of SEQ ID NO: 3. The use of these compounds decreases in a significant manner the expression on TCTP in these PC cells (FIG. 4).

Figure 12:
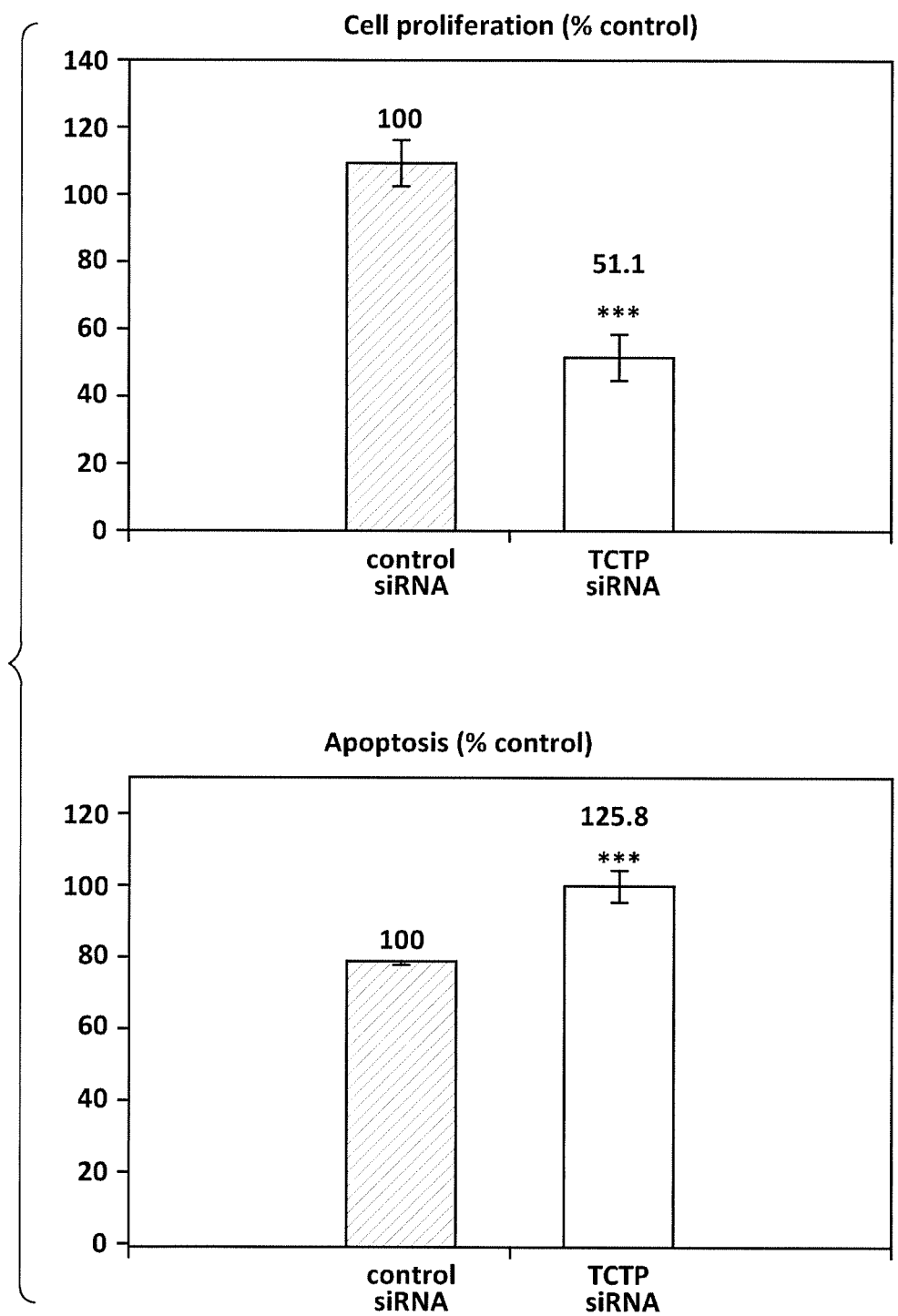
FIG. 12 illustrates the impact of a TCTP siRNA on proliferation and apoptosis of PC3 cells.

Anti-proliferative and Pro-apoptotic Effects of Developed TCTP siRNA in CRPC Cell Line PC3 cells were transfected with a TCTP siRNA of SEQ ID NO: 3. Cell proliferation and apoptosis were studied using respectively MTT (3-(4,5-dimethylthiazol-2-yl)-2,5-diphenyl tetrazolium bromure) assay and flow cytometry. The use of this siRNA significantly decreased (48.1%) the proliferation of PC3 cells and conversely increased the percentage (25.8) of apoptotic cells (FIG. 12).

Figure 13:
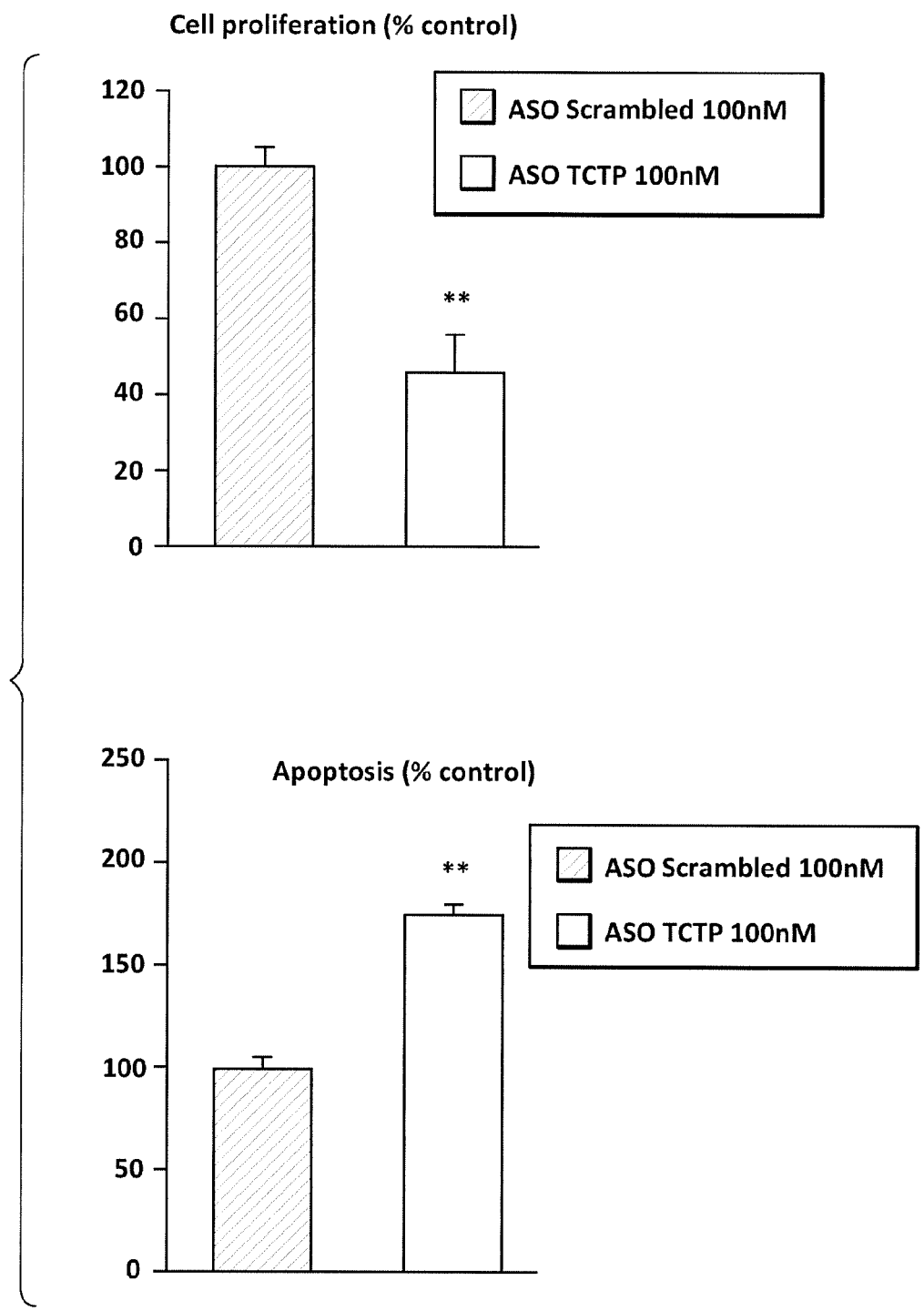
FIG. 13 illustrates the impact of a TCTP ASO on proliferation and apoptosis of PC3 cells.

Anti-proliferative and Pro-apoptotic Effects of Developed ASO TCTP in CRPC PC3 Cell Line PC3 cells were transfected with a TCTP ASO of SEQ ID NO: 2. Cell proliferation and apoptosis were studied using respectively MTT assay and flow cytometry. The use of this ASO significantly decreased (58%) the proliferation of PC3 cells and conversely increased the percentage (70) of apoptotic cells (FIG. 13) via activation of caspase-3.

In Vivo Experiments of the Additive Anticancer Activity of TCTP Inhibition and Docetaxel Treatment in PC3 Xenografted Nude Mice TCTP inhibition was evaluated in nude mice xenografted with the PC3 CRPC cell line. The animals were treated in an everyday basis and for a period of two months by peritoneal injection of ASO or control TCTP once their tumor volume was 200-300 mm$^3$. In order to evaluate the additive anticancer activity of ASO TCTP, mice were treated with docetaxel (33 mg/kg) by peritoneal injection three times per week for one week prior to ASO or control TCTP injections. For all experiments, the average tumor volume was measured once a week.

Treatment of mice with ASO TCTP induced maintenance of tumor volume at 500 mm$^3$ as compared to control TCTP (ASO scrambled) which measured over 1500 mm$^3$ at the 10th week of treatment (FIG. 8). It was observed that treatment with docetaxel followed by ASO TCTP firstly induced a decrease of tumor volume then maintenance of tumor volume at 100 mm$^3$. Conversely, tumor volumes continued to increase after the 9th week of treatment with control TCTP.

These results demonstrate the significant additive anticancer effect of ASO TCTP when combined with a chemotherapeutic agent such as the docetaxel antimitotic agent.

Example 12

Hsp27 Association with TCTP Involves its C-Terminal Region and Depends on the Unphosphorylated State of the Chaperone Materials and Methods
Hsp27 Deletion and Phosphorylation Mutant's Transfection.

Histidine-tagged (His-tag) Hsp27 WT and three deletion mutants (N1, N2 and C1) in pcDNA4 containing His-tag epitope at N-terminal of the inserted fragment (Al-Madhoun A S. et al., 2007, Mol Cell Endocrinol; 270) were kindly provided by Pr O'Brien (Ottawa University, Ontario, Canada). The phosphorylation mutants (3D and 3A) in pcDNA3 containing hemagglutinin-tag (HA-tag) at N-terminal of the inserted fragment were kindly provided by Dr. Carmen Garrido (INSERM U866, Faculty of Medicine and Pharmacy, Dijon, France). LNCaP cells were transfected with 10 mg WT, deletion or phosphorylation mutants using Fugene reagent (Roche Diagnostics GmbH, Mannheim, Germany) according to the manufacturer's instructions. Cleared lysates were obtained 48 h post transfection according to our previous experiments (Rocchi P, et al., 2004, Cancer Res; 64: 6595-6602).

Immunoprecipitation.

Cleared lysates with adjusted protein concentration (Protein assay, BioRad, Marnes-la-Coquette, France) were used for immunoprecipitation with rabbit anti-TCTP antibody (Abcam Inc., Cambridge, UK) and rabbit IgG (rIgG; Millipore, Billerica, Mass., USA) at 4° C. Immune complexes were precipitated following 1 h incubation with 30 µl true blot rabbit beads (eBiosciences SAS, Paris, France) at 4° C. Complexes were suspended in protein sample buffer (Bio-Rad) and boiled for 5 min Western Blot analysis was performed as previously described (Rocchi P, et al., 2004, Cancer Res; 64: 6595-6602) with secondary anti-mouse and anti-rabbit true blot HRP-conjugated antibodies (eBiosciences).

Results

In order to analyze Hsp27-TCTP interaction, we used Hsp27 deletion mutants previously described by Al-Madhoun (Al-Madhoun A S et al., 2007, Mol Cell Endocrinol; 270: 33-42). The C-terminal mutant Hsp27 N1 having the aminoacids 1 to 93 of sequence SEQ ID NO: 16, lacks part of the α-crystallin domain, believed to mediate oligomerization of Hsp27 (Ciocca D R. et al., 1993 J Natl Cancer Inst; 85: 1558-1570). The Hsp27 N2 mutant having the aminoacids 1 to 173 of sequence SEQ ID NO: 16 lacks the flexible domain (IXI box) at the C-terminal, believed to be involved in the formation of multiple inter-subunit interactions (Lelj-Garolla B. et al., 2005 J Mol Biol; 345: 631-642). Finally, the N-terminal mutant, Hsp27 C1 having the aminoacids 93 to 205 of sequence SEQ ID NO: 16, lacks the hydrophobic WDPF domain and the major phosphorylation sites necessary for interacting with other proteins and molecular chaperone function (Lindquist S. et al., 1988, Annu Rev Genet; 22: 631-677).

Immunoprecipitation of TCTP followed by immunoblot analysis with anti-polyhistidine antibody was performed on LNCaP cells transiently transfected with constructs encoding histidine-tagged wild type (WT) or Hsp27 truncated mutant forms (N1, N2 and C1). TCTP was able to interact with WT-Hsp27 and C1, while no or weak interaction was observed with N1 and N2, respectively.

Interestingly, only transfection with C1 protected LNCaP and REG cells from docetaxel-induced apoptosis (a protection similar to that observed with WT-Hsp27). In contrast, transfection with N1 or N2 sensitized LNCaP and REG cells to docetaxel, compared with cells transfected with WT-Hsp27. These results suggest that cytoprotection induced by Hsp27 in LNCaP cells seems to involve TCTP interaction.

Phosphorylation of the 3 Serine (Ser) residues of Hsp27 (position 15, 78 and 82), has been shown to modulate Hsp27 functions (Garrido C. et al., 2002 Cell Death Differ; 9: 483-485). To analyze the effect of Hsp27 phosphorylation on its association with TCTP, we used two phospho-mutants (3D and 3A) of Hsp27. The 3D mutant has the three Ser residues 15, 78 and 82 of sequence SEQ ID NO: 16 replaced by aspartates that mimic the constitutively phosphorylated protein. The 3A mutant has the three Ser residues 15, 78 and 82 of sequence SEQ ID NO: 16 replaced by alanines that mimic the constitutively dephosphorylated protein. We found that the constitutively dephosphorylated 3A mutant bound to TCTP more efficiently than the phosphorylatable 3D mutant. Thus, Hsp27 phosphorylation considerably decreases TCTP interaction. Surprisingly, we found no difference on LNCaP cell chemoresistance after transfection with WT, 3D or 3A. This result indicates that the phosphorylation state of Hsp27 is important for interactions with its partner proteins. Hsp27 seems to interact with specifics partners involved in the cytoprotection of Hsp27 in both phosphorylation states.

The invention claimed is:

1. A nucleic acid targeting an mRNA encoding Translationally-Controlled Tumor Protein (TCTP), wherein said nucleic acid:
   is capable of reducing the amount of TCTP in cells;
   is an antisense oligonucleotide;
   comprises 18 to 35 consecutive nucleotides of a sequence complementary to said mRNA;
   is chemically modified to increase the stability and/or therapeutic efficiency; and
   comprises a fragment of at least 10 consecutive nucleotides of a sequence of SEQ ID NO: 2, or a fragment of at least 18 consecutive nucleotides of a sequence of SEQ ID NO: 14, or a fragment of at least 15 consecutive nucleotides of a sequence of SEQ ID NO: 15.

2. A nucleic acid targeting an mRNA encoding Translationally-Controlled Tumor Protein (TCTP), wherein said nucleic acid:
   is capable of reducing the amount of TCTP in cells;
   is an antisense oligonucleotide or an interfering RNA (iRNA);
   comprises 20 to 35 consecutive nucleotides of a sequence complementary to said mRNA;

is chemically modified to increase the stability and/or therapeutic efficiency; and comprises or consists of a sequence of SEQ ID NO: 2, a sequence of SEQ ID NO: 3, a sequence of SEQ ID NO: 14 or a sequence of SEQ ID NO: 15.

3. The nucleic acid targeting an mRNA encoding Translationally-Controlled Tumor Protein (TCTP), according to claim 2, wherein said nucleic acid:

comprises phosphorothioate derivative(s), MOE-modified oligonucleotide(s) and/or lipid-modified oligonucleotide(s).

4. The nucleic acid targeting an mRNA encoding Translationally-Controlled Tumor Protein (TCTP), according to claim 2, wherein said nucleic acid:

comprises 21 to 35 consecutive nucleotides of a sequence complementary to said mRNA;

is an interfering RNA (iRNA) comprising non-nucleotide material and/or non-standard nucleotide(s); and comprises or consists of sequence SEQ ID NO: 3.

5. A nucleic acid targeting an mRNA encoding Translationally-Controlled Tumor Protein (TCTP), wherein said nucleic acid:

is capable of reducing the amount of TCTP in cells;

targets a sequence overlapping with nucleotides 153 to 173 of SEQ ID NO: 5;

comprises 20 to 35 consecutive nucleotides of a sequence complementary to said mRNA; and is an interfering RNA (iRNA).

6. A method for treating or preventing cancer comprising the step of administering an effective amount of a nucleic acid targeting an mRNA encoding Translationally-Controlled Tumor Protein (TCTP) to an individual in need thereof, wherein said nucleic acid is a nucleic acid according to any one of claims 1, 2, and 5, and wherein said cancer is a hormone-independent cancer or chemo-resistant prostate cancer.

7. The method of claim 6, wherein said cancer is a hormone-independent cancer or chemo-resistant cancer.

8. The method of claim 6, wherein said nucleic acid is administered to said individual simultaneously or sequentially with a second anti-cancer agent.

9. The method of claim 8, wherein said second anti-cancer agent is selected from the group consisting of an antimitotic agent, an alkylating agent, an antimetabolite, a topoisomerase inhibitor, an aromatase inhibitor, a signaling inhibitor, a monoclonal antibody, a biologic response modifier, a differentiating agent and an agent that blocks blood vessel formation.

10. The method of claim 8, wherein said second anti-cancer agent is docetaxel.

11. The method of claim 6, wherein administration of said nucleic acid to the individual is simultaneously or subsequently associated with radiation therapy, surgery and/or androgen withdrawal.

12. The method of claim 6, wherein said method further comprises the step of restoring sensibility of said individual to hormone- and/or chemo-therapy.

* * * * *

SEQUENCE LISTING

```
<160> NUMBER OF SEQ ID NOS: 40

<210> SEQ ID NO 1
<211> LENGTH: 172
<212> TYPE: PRT
<213> ORGANISM: Homo sapiens

<400> SEQUENCE: 1

Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
            20                  25                  30

Gly Lys Met Val Ser Arg Thr Glu Gly Asn Ile Asp Asp Ser Leu Ile
        35                  40                  45

Gly Gly Asn Ala Ser Ala Glu Gly Pro Glu Gly Glu Gly Thr Glu Ser
    50                  55                  60

Thr Val Ile Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Phe Ile Gly Glu Asn Met Asn Pro Asp Gly
    130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170

<210> SEQ ID NO 2
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 2
accaatgagc gagtcatcaa                                                 20

<210> SEQ ID NO 3
<211> LENGTH: 21
<212> TYPE: RNA
<213> ORGANISM: Artificial
<220> FEATURE:
<223> OTHER INFORMATION: Synthetic siRNA targeting TCTP

<400> SEQUENCE: 3
aacccguccg cgaucucccg g                                               21

<210> SEQ ID NO 4
<211> LENGTH: 19
<212> TYPE: DNA
<213> ORGANISM: Artificial
```

```
<220> FEATURE:
<223> OTHER INFORMATION: Synthetic scrambled oligonucleotide

<400> SEQUENCE: 4
cgtgtaggta cggcagatc                                                    19

<210> SEQ ID NO 5
<211> LENGTH: 829
<212> TYPE: DNA
<213> ORGANISM: Homo sapiens
<220> FEATURE:
<221> NAME/KEY: misc_feature
<222> LOCATION: (153)..(173)
<223> OTHER INFORMATION: Region targeted by the siRNA of SEQ ID NO: 3
<220> FEATURE:
<221> NAME/KEY: misc_feature
<222> LOCATION: (221)..(240)
<223> OTHER INFORMATION: Region targeted by the antisense
      oligonucleotide of SEQ ID NO: 2

<400> SEQUENCE: 5 cccccccgagc gccgctccgg ctgcaccgcg ctcgctccga gtttcaggct cgtgctaagc       60
tagcgccgtc gtcgtctccc ttcagtcgcc atcatgatta tctaccggga cctcatcagc      120
cacgatgaga tgttctccga catctacaag atccgggaga tcgcggacgg gttgtgcctg      180
gaggtggagg ggaagatggt cagtaggaca gaaggtaaca ttgatgactc gctcattggt      240
ggaaatgcct ccgctgaagg ccccgagggc gaaggtaccg aaagcacagt aatcactggt      300
gtcgatattg tcatgaacca tcacctgcag gaaacaagtt tcacaaaaga agcctacaag      360
aagtacatca aagattacat gaaatcaatc aaagggaaac ttgaagaaca gagaccagaa      420
agagtaaaac cttttatgac aggggctgca gaacaaatca agcacatcct tgctaatttc      480
aaaaactacc agttctttat tggtgaaaac atgaatccag atggcatggt tgctctattg      540
gactaccgtg aggatggtgt gaccccatat atgatttttct ttaaggatgg tttagaaatg      600
gaaaaatgtt aacaaatgtg gcaattattt tggatctatc acctgtcatc ataactggct      660
tctgcttgtc atccacacaa caccaggact taagacaaat gggactgatg tcatcttgag      720
ctcttcattt attttgactg tgatttattt ggagtggagg cattgttttt aagaaaaaca      780
tgtcatgtag gttgtctaaa aataaaatgc atttaaactc atttgagag                  829

<210> SEQ ID NO 6
<211> LENGTH: 20
<212> TYPE: DNA
<213> ORGANISM: Artificial
<220> FEATURE:
<223> OTHER INFORMATION: Synthetic primer

<400> SEQUENCE: 6
aaccccggat cggactacta                                                   20

<210> SEQ ID NO 7
<211> LENGTH: 20
<212> TYPE: DNA
<213> ORGANISM: Artificial
<220> FEATURE:
<223> OTHER INFORMATION: Synthetic primer

<400> SEQUENCE: 7
aataagctct agagggccgc                                                   20
```

```
<210> SEQ ID NO 8
<211> LENGTH: 23
<212> TYPE: DNA
<213> ORGANISM: Artificial
<220> FEATURE:
<223> OTHER INFORMATION: Synthetic primer

<400> SEQUENCE: 8
gaaagcacag taatcactgg tgt                                              23

<210> SEQ ID NO 9
<211> LENGTH: 21
<212> TYPE: DNA
<213> ORGANISM: Artificial
<220> FEATURE:
<223> OTHER INFORMATION: Synthetic primer

<400> SEQUENCE: 9
gcagcccctg tcataaaagg t                                                21

<210> SEQ ID NO 10
<211> LENGTH: 20
<212> TYPE: DNA
<213> ORGANISM: Artificial
<220> FEATURE:
<223> OTHER INFORMATION: Synthetic primer

<400> SEQUENCE: 10
ctaccacatc caaggaaggc                                                  20

<210> SEQ ID NO 11
<211> LENGTH: 20
<212> TYPE: DNA
<213> ORGANISM: Artificial
<220> FEATURE:
<223> OTHER INFORMATION: Synthetic primer

<400> SEQUENCE: 11
ttttcgtcac tacctccccg                                                  20

<210> SEQ ID NO 12
<211> LENGTH: 20
<212> TYPE: DNA
<213> ORGANISM: Artificial
<220> FEATURE:
<223> OTHER INFORMATION: Synthetic primer

<400> SEQUENCE: 12
gggacgcggc gctcggtcat                                                  20

<210> SEQ ID NO 13
<211> LENGTH: 21
<212> TYPE: DNA
<213> ORGANISM: Artificial
<220> FEATURE:
<223> OTHER INFORMATION: Synthetic primer

<400> SEQUENCE: 13
cagcagcaga gtatttatca t                                                21

<210> SEQ ID NO 14
<211> LENGTH: 20
<212> TYPE: DNA
<213> ORGANISM: Artificial
<220> FEATURE:
<223> OTHER INFORMATION: Synthetic antisense oligonucleotide targeting
      TCTP
```

<400> SEQUENCE: 14
aacttgtttc ctgcaggtga                                               20

<210> SEQ ID NO 15
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 15
tggttcatga caatatcgac                                               20

<210> SEQ ID NO 16
<211> LENGTH: 205
<212> TYPE: PRT
<213> ORGANISM: Homo sapiens

<400> SEQUENCE: 16

Met Thr Glu Arg Arg Val Pro Phe Ser Leu Leu Arg Gly Pro Ser Trp
1               5                   10                  15

Asp Pro Phe Arg Asp Trp Tyr Pro His Ser Arg Leu Phe Asp Gln Ala
                20                  25                  30

Phe Gly Leu Pro Arg Leu Pro Glu Glu Trp Ser Gln Trp Leu Gly Gly
            35                  40                  45

Ser Ser Trp Pro Gly Tyr Val Arg Pro Leu Pro Pro Ala Ala Ile Glu
        50                  55                  60

Ser Pro Ala Val Ala Ala Pro Ala Tyr Ser Arg Ala Leu Ser Arg Gln
65                  70                  75                  80

Leu Ser Ser Gly Val Ser Glu Ile Arg His Thr Ala Asp Arg Trp Arg
                85                  90                  95

Val Ser Leu Asp Val Asn His Phe Ala Pro Asp Glu Arg Thr Val Lys
                100                 105                 110

Thr Lys Asp Gly Val Val Glu Ile Ser Gly Lys His Glu Glu Leu Gln
            115                 120                 125

Asp Glu His Gly Tyr Ile Ser Arg Cys Phe Thr Arg Lys Tyr Thr Leu
        130                 135                 140

Pro Pro Gly Val Asp Pro Thr Gln Val Ser Ser Ser Leu Ser Pro Glu
145                 150                 155                 160

Gly Thr Leu Thr Val Glu Ala Pro Met Pro Lys Leu Ala Thr Gln Ser
                165                 170                 175

Asn Glu Ile Thr Ile Pro Val Thr Phe Glu Ser Arg Ala Gln Leu Gly
                180                 185                 190

Gly Pro Glu Ala Ala Lys Ser Asp Glu Thr Ala Ala Lys
            195                 200                 205

<210> SEQ ID NO 17
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 17
taatcatgat ggcgactgaa                                               20

```
<210> SEQ ID NO 18
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 18
gctgatgagg tcccggtaga                                              20

<210> SEQ ID NO 19
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 19
tcggagaaca tctcatcgtg                                              20

<210> SEQ ID NO 20
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 20
caggcacaac ccgtccgcga                                              20

<210> SEQ ID NO 21
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 21
accatcttcc cctccacctc                                              20

<210> SEQ ID NO 22
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 22
tgttaccttc tgtcctactg                                              20

<210> SEQ ID NO 23
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 23
ccttcagcgg aggcatttcc                                              20
```

```
<210> SEQ ID NO 24
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 24
cagtaccttc gccctcgggg                                                  20

<210> SEQ ID NO 25
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 25
accagtgatt actgtgcttt                                                  20

<210> SEQ ID NO 26
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 26
cttgtaggct tcttttgtga                                                  20

<210> SEQ ID NO 27
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 27
atgtaatctt tgatgtactt                                                  20

<210> SEQ ID NO 28
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 28
gtttcccttt gattgatttc                                                  20

<210> SEQ ID NO 29
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 29
ttctggtctc tgttcttcaa                                                  20
```

```
<210> SEQ ID NO 30
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 30
ataaagaact ggtagttttt                                                     20

<210> SEQ ID NO 31
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 31
ctggattcat gttttcacca                                                     20

<210> SEQ ID NO 32
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 32
caatagagca accatgccat                                                     20

<210> SEQ ID NO 33
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 33
acaccatcct cacggtagtc                                                     20

<210> SEQ ID NO 34
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 34
agaaaatcat atatggggtc                                                     20

<210> SEQ ID NO 35
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 35
catttctaaa ccatccttaa                                                     20
```

```
<210> SEQ ID NO 36
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 36
ttaacatttc tccatttcta                                              20

<210> SEQ ID NO 37
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 37
tctcccggat cttgtagatg                                              20

<210> SEQ ID NO 38
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 38
gtcataaaag gttttactct                                              20

<210> SEQ ID NO 39
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 39
tgatttgttc tgcagcccct                                              20

<210> SEQ ID NO 40
<211> LENGTH: 20
<212> TYPE: DNA
<213> ORGANISM: Artificial
<220> FEATURE:
<223> OTHER INFORMATION: Synthetic antisense oligonucleotide targeting
      TCTP

<400> SEQUENCE: 40
gaaattagca aggatgtgct                                              20
```